United States Patent
Seminowicz et al.

(10) Patent No.: US 11,672,474 B2
(45) Date of Patent: Jun. 13, 2023

(54) METHOD FOR PREDICTING PAIN SENSITIVITY

(71) Applicants: University of Maryland, Baltimore, Baltimore, MD (US); The University of Birmingham, Birmingham (GB)

(72) Inventors: David A. Seminowicz, Baltimore, MD (US); Andrew J. Furman, Towson, MD (US); Ali Mazaheri, Birmingham (GB)

(73) Assignees: University of Maryland, Baltimore, Baltimore, MD (US); The University of Birmingham, Birmingham (GB)

( * ) Notice: Subject to any disclaimer, the term of this patent is extended or adjusted under 35 U.S.C. 154(b) by 332 days.

(21) Appl. No.: 16/864,204

(22) Filed: May 1, 2020

(65) Prior Publication Data
US 2020/0253540 A1 Aug. 13, 2020

Related U.S. Application Data

(63) Continuation-in-part of application No. PCT/US2018/058889, filed on Nov. 2, 2018.

(60) Provisional application No. 62/580,503, filed on Nov. 2, 2017.

(51) Int. Cl.
*A61B 5/00* (2006.01)
*A61B 5/30* (2021.01)
*A61B 5/375* (2021.01)
*A61B 5/377* (2021.01)

(52) U.S. Cl.
CPC ............ *A61B 5/483* (2013.01); *A61B 5/30* (2021.01); *A61B 5/375* (2021.01); *A61B 5/377* (2021.01); *A61B 5/6848* (2013.01)

(58) Field of Classification Search
CPC ............ A61B 5/369; A61B 5/483; A61B 5/30; A61B 5/6848; A61B 5/377; A61B 5/4824; A61B 5/375
See application file for complete search history.

(56) References Cited

U.S. PATENT DOCUMENTS

2014/0276188 A1* 9/2014 Jardin ................. A61B 5/7267
600/544

FOREIGN PATENT DOCUMENTS

CN 101677775 B * 8/2012 ........... A61B 5/0476

OTHER PUBLICATIONS

Malkin, Nursing, Apr. 7, 2009, "Reducing pain when giving intramuscular injections" (Year: 2009).*

(Continued)

*Primary Examiner* — Scott S Trotter
(74) *Attorney, Agent, or Firm* — Benjamin Aaron Adler

(57) ABSTRACT

Provided herein are methods to predict pain sensitivity and pain intensity to prolonged pain in a subject. Electroencephalograms are recorded in a pain-free state or, alternatively, in a pain-free state and after applying a prolonged pain stimulus in a prolonged pain state. Pain-free and prolonged pain peak alpha frequencies or ΔPAF are measured. These values correlate negatively with the likelihood of increased pain sensitivity and increased pain intensity. Also provided is a method for predicting a likelihood of chronic pain in a subject after a medical procedure and designing a plan to treat the chronic pain.

23 Claims, 21 Drawing Sheets

(56) References Cited

OTHER PUBLICATIONS

Rony-Rueven Nir et al., May 9, 2010, ScienceDirect.com, "Pain assessment by continuous EEG: Association between subjective perception of tonic pain and peak frequency of alpha oscillations during stimulation and at rest" (Year: 2010).*
John Joseph et al., Oct. 30, 2013, JBC Papers in Press, "Carboxyl-terminal Domain of Transient Receptor Potential Vanilloid 1 Contains Distinct Segments Differentially Involved in Capsaicin- and Heat-induced Desensitization" (Year: 2013).*
P. Chang et al., Dec. 2016, Cerebral Cortex, "The Development of Nociceptive Network Activity in the Somatosensory Cortex of Freely moving rat pups" (Year: 2016).*
Lorincz et al., Cellular Dynamics of Cholinergically Induced (8-13 Hz) Rhythms in Sensory Thalamic Nuclei In Vitro. J. Neurosci. 28:660-671, 2008.
Lorincz et al., Temporal Framing of Thalamic Relay-Mode Firing by Phasic Inhibition during the Alpha Rhythm. Neuron 63:683-696, 2009.
Lotsch et al., Pattern of neuropathic pain induced by topical capsaicin application in healthy subjects. Pain 156:405-414, 2015.
Malloy KM and Milling LS, The effectiveness of virtual reality distraction for pain reduction: A systematic review. Clinical psychology review, 30(8): 1011-1018, 2010.
Mathewson et al., To See or Not to See: Prestimulus Phase Predicts Visual Awareness. J. Neurosci. 29:2725-2732, 2009.
Mazaheri et al., Prestimulus Alpha and Mu Activity Predicts Failure to Inhibit Motor Responses. Hum. Brain Ma 30:1791-1800, 2009.
Mazaheri et al., Functional Disconnection of Frontal Cortex and Visual Cortex in Attention-Deficit/Hyperactivity Disorder. Biological Psychiatry 67:617-623,2010.
Mazaheri et al., Region-specific modulations in oscillatory alpha activity serve to facilitate processing in the visual and auditory modalities. NeuroImage 87:356-362, 2014.
Moran et al., Peak frequency in the theta and alpha bands correlates with human working memory capacity. Front Hum Neurosci 4, 2010.
Moritz AR and Henriques FC, Studies of Thermal Injury. Am J Pathol 23:695-720, 1947.
Naert et al., Characterization of a novel model of tonic heat pain stimulation in healthy volunteers. Pain, 138 (1):163-171, 2008.
Nielsen et al., Characterizing individual differences in heat-pain sensitivity. Pain, 119(1-3):65-7 4, 2005.
Nir et al., Pain assessment by continuous EEG: Association between subjective perception of tonic pain and peak frequency of alpha oscillations during stimulation and at rest. Brain Research 1344:77-86, 2010.
Nir et al., Tonic pain and continuous EEG: Prediction of subjective pain perception by alpha-1 power during stimulation and at rest. Clinical Neurophysiology 123:605-612, 2012.
Oldfield RC, The Assessment and Analysis of Handedness: The Edinburgh Inventory. Neuropsychologia, 9 (1):97-113, 1971.
Oostenveld et al., The five percent electrode system for high-resolutionEEG and ERP measurements. Clinical Neurophysiology 112:713-719, 2001.
Peng et al., Subjective pain perception mediated by alpha rhythms. Biological Psychology 109:141-150, 2015.
Perrin et al., Spherical splines for scalp potential and current density mapping. Electroencephalography and clinical neurophysiology, 72(2): 184-187, 1989.
Pfurtscheller et al., Event-related synchronization ( ERS) in the alpha band—an electrophysiological correlate of cortical idling: A review. Inter Journal of Psychophysiology 24:39-46, 1996.
Ploner et al., Oscillatory activity reflects the excitability of the human somatosensory system. NeuroImage 32:1231-1236, 2006.
Ploner et al., Brain Rhythms of Pain. Trends in Cognitive Sciences 21:100-110, 2017.
Posthuma et al., Are Smarter Brains Running Faster? Heritability of Alpha Peak Frequency, IQ, and Their Interrelation. Behav Genet 31:567-579, 2001.
Price et al., A comparison of pain measurement characteristics of mechanical visual analogue and simple numerical rating scales. Pain, 56(2):217-226, 1994.
Romei et al., Resting electroencephalogram alpha-power over posterior sites indexes baseline visual cortex excitability. Neuroreport 19, 203-208, 2008.
Rouder JN, Bayesian t tests for accepting and rejecting the null hypothesis. Psychonomic bulletin & review, 16 (2):225-237, 2009.
Samaha et al., Top-down control of the phase of alpha-band oscillations as a mechanism for temporal prediction. PNAS 112:8439-8444, 2015.
Sarnthein, et al., Increased EEG power and slowed dominant frequency in patients with neurogenic pain. Brain, 129(1):55-64, 2005.
Schabrun et al., Motor Cortex Reorganization and Impaired Function in the Transition to Sustained Muscle Pain. Cerebral Cortex, 26(5): 1878-1890, 2015.
Scheeringa et al., Neuronal Dynamics Underlying High- and Low-Frequency EEG Oscillations Contribute Independently to the Human BOLD Signal. Neuron 69, 572-583, 2011 a.
Scheeringa et al., Modulation of Visually Evoked Cortical fMRI Responses by Phase of Ongoing Occipital Alpha Oscillations. The Journal of Neuroscience 31:3813-3820, 2011 b.
Seminowicz et al., Cognitive modulation of pain-related brain responses depends on behavioral strategy. Pain, 112 (1-2):48-58, 2004.
Smit et al., Genetic variation of individual alpha frequency (IAF). International Journal of Psychophysiology 61, 235-243, 2006.
Sokolova M and Lapalme G, A systematic analysis of performance measures for classification tasks. Information processing & management, 45(4):427-437, 2009.
Walls et al., Sex differences in the perception of pain fromtopical capsaicin. The Journal of Pain 18:S27-S28, 2017.
Walton et al., Abnormal thalamocortical activity in patients with Complex Regional Pain Syndrome (CRPS) Type I. Pain 150:41-51,2010.
Ali et al., Secondary hyperalgesia to mechanical but not heat stimuli following a capsaicin injection in hairy skin. Pain, 68:401-411, 1996.
Backonja, et al., Tonic changes in alpha power during immersion of the hand in cold water. Electroencephalography and Clinical Neurophysiology 79:192-203, 1991.
Baliki et al., Corticostriatal functional connectivity predicts transition to chronic back pain. Nature Neuroscience 15:11171119,2012.
Baron R, Neuropathic Pain: A Clinical Perspective. Sensory Nerves, (Springer, Berlin, Heidelberg), 3-30, 2009.
Baum C et al., Prediction of experimental pain sensitivity by attention to pain-related stimuli in healthy individuals. Perceptual and motor skills, 112(3), 926-946, 2011.
Baumann et al., Neurogenic Hyperalgesia: The Search for the Primary Cutaneous Merent Fibers That Contribute to Capsaicin-Induced Pain and Hyperalgesia. Journal of Neurophysiology 66, 212-227, 1991.
Bazanova et al., Interpreting EEG alpha activity. Neuroscience & Biobehavioral Reviews 44:94-110, 2014.
Bell AJ and Sejnowski TJ, An Information-Maximization Approach to Blind Separation and Blind Deconvolution. Neural Computation 7:1129-1159, 1995.
Bergin, MJG et al., Movement Evoked Pain and Mechanical Hyperalgesia after Intramuscular Injection of Nerve Growth Factor: A Model of Sustained Elbow Pain Pain Medicine, 16(11 ), 2180-2191, 2015.
Brotzner et al., Progesterone-associated increase in ERP amplitude correlates with an improvement in performance in a spatial attention paradigm. Brain Res. 1577: 36-44, 2015.
Busch et al., The Phase of Ongoing EEG Oscillations Predicts Visual Perception. J. Neurosci. 29, 7869-7876, 2009.
Campbell et al., Polymorphisms in the GTP cyclohydrolase gene (GCH1) are associated with ratings of capsaicin pain. Pain, 141 (1-2): 114-118, 2009.

(56) References Cited

OTHER PUBLICATIONS

Cecere et al., Individual Differences in Alpha Frequency Drive Crossmodal Illusory Perception. Current Biology 25:231-235, 2015.
Llinas et al., Thalamocortical dysrhythmia: A neurological and neuropsychiatric syndrome characterized by magnetoencephalography. PNAS, 96(26): 15222-5227, 1999.
Culp et al., Heat and mechanical hyperalgesia induced by capsaicin cross modality threshold modulation in human c nociceptors. Brain 112:1317-1331,1989.
De Vries et al., A ltered resting state EEG in chronic pancreatitis patients: toward a marker for chronic pain. Journal of Pain Research 6:815-824, 2013.
Delorme A and Makeig S, EEGLAB: an open source toolbox for analysis of single-trial EEG dynamics including independent component analysis. Journal of Neuroscience Methods 134:9-21, 2004.
Diatchenko et al., Genetic basis for individual variations in pain perception and the development of a chronic pain condition. Human Molecular Genetics, 14(1 ): 135-143, 2005.
Dirks et al., The Heat/Capsaicin Sensitization Model: A Methodologic Study. The Journal of Pain, 4(3):122-128, 2003.
Foxe et al., Parieto-occipital ~10Hz activity reflects anticipatory state of visual attention mechanisms. Neuroreport, 9:3929-3933, 1998.
Foxe JJ and Snyder AC, The role of alpha-band brain oscillations as a sensory suppression mechanism during selective attention. Front Psychol 2, 2011.
Furman et al., Cerebral peak alpha frequency predicts individual differences in pain sensitivity. Neuroimage, 167:203-210, 2018.
Furman et al., Sensorimotor peak alpha frequency is a reliable biomarker of pain sensitivity. BioRxiv, 613299, 2019.
Goffaux et al., Pain relief through expectation supersedes descending inhibitory deficits in fibromyalgia patients. Pain, 145(1-2): 18-23, 2009.
Goldman et al., Simultaneous EEG and fMRI of the alpha rhythm. Neuroreport 13:2487-2492, 2002.
Grandy et al., Peak individual alpha frequency qualifies as a stable neurophysiological trait marker in healthy younger and older adults. Psychophysiol 50:570-582, 2013.
Hah, JM, Factors Associated With Acute Pain Estimation, Postoperative Pain Resolution, Opioid Cessation, and Recovery Secondary Analysis of a Randomized Clinical Tr. JAMA network open, 2(3):e190168-e190168, 2019.
Hashemi et al., Characterizing population EEG dynamics throughout adulthood. ENeuro 3, eNEUR0.0275-16.2016, 2016.
Hughes SW and Crunelli V, Thalamic Mechanisms of EEG Alpha Rhythms and Their Pathological Implications. Neuroscientist 11:357-372, 2005.
Lannetti, et al., Operculoinsular cortex encodes pain intensity at the earliest stages of cortical processing as indicated by amplitude of laser-evoked potentials in humans. Neuroscience, 131(1): 199-208, 2005.
Jann et al., Association of individual resting state EEG alpha frequency and cerebral blood flow. NeuroImage 51:365-372, 2010.
Jann et al., Linking Brain Connectivity Across Different Time Scales with Electroencephalogram, Functional Magnetic Resonance Imaging, and Diffusion Tensor Imaging. Brain Connectivity 2:11-20, 2012.
Jensen O and Mazaheri A, Shaping functional architecture by oscillatory alpha activity: gating by inhibition. Front Hum Neurosci 4, 2010.
Jin et al., Alpha EEG predicts visual reaction time. Int. J. Neurosci. 116:1035-1044,2006.
Kalauokalani et al., Lessons from a Trial of Acupuncture and Massage for Low Back Pain. Spine, 26(13): 1418-1424, 2001.
Katz et al., Acute pain after thoracic surgery predicts long-term post-thoracotomy pain. Clin J Pain 12:50-55, 1996.
Keel J C et al., Letter to the Editor: A safety screening questionnaire for transcranial magnetic stimulation. Neurophysiology, 112(4):720-720, 2001.
Klimesch et al., Alpha Frequency, Cognitive Load and Memory Performance. Brain Topogr 5:241-251, 1993.
Klimesch et al., EEG alpha oscillations: The inhibition-timing hypothesis. Brain Research Reviews 53:63-88, 2007.
Klimesch W, EEG alpha and theta oscillations reflect cognitive and memory performance: a review and analysis. Brain Res Brain Res.Rev. 29:169-195, 1999.
Klimesch W, Alpha-band oscillations, attention, and controlled access to stored information. Trends in Cognitive Sciences 16:606-617, 2012.
Koenig et al., Two-Week Test-Retest Stability of the Cold Pressor Task Procedure at two different Temperatures as a Measure of Pain Threshold and Tolerance. Pain Practice, 14(3): E 126-E 135, 2014.
Lamotte et al., Pain, Hyperalgesia and Activity In Nociceptive C Units in Humans after Intradermal Injection of Capsaicin. The Journal of Physiology 448:749-764, 1992.
Lewin et al., Neonatal Anti-NGF Treatment Reduces the A-delta and C-Fibre Evoked Vasodilator Responses in Rat Skin: Evidence That Nociceptor Afferents Mediate Antidromic Vasodilatation. European Journal of Neuroscience, 4 (12):1213-1218, 1992.
Lim J and Dinges DF, Annals of the New York Academy of Sciences, 1129(1 ):305-322, 2008.
Lim et al., Increased Low- and High-Frequency Oscillatory Activity in the Prefrontal Cortex of Fibromyalgia Patients. Front Hum Neurosci 10, 2016.
Lipton, et al., In Joint European Conference on Machine Learning and Knowledge Discovery in Databases. Springer, Berlin, Heidelberg, 225-239, 2014.
Liu et al., The Human Capsaicin Model of Allodynia and Hyperalgesia: Sources of Variability and Methods for Reduction. Journal of Pain and Symptom Management, 16(1 ): 10-20, 1998.
Llinas et al., Rhythmic and dysrhythmic thalamocortical dynamics: GABA systems and the edge effect. Trends in Veurosciences 28:325-333, 2005.

\* cited by examiner

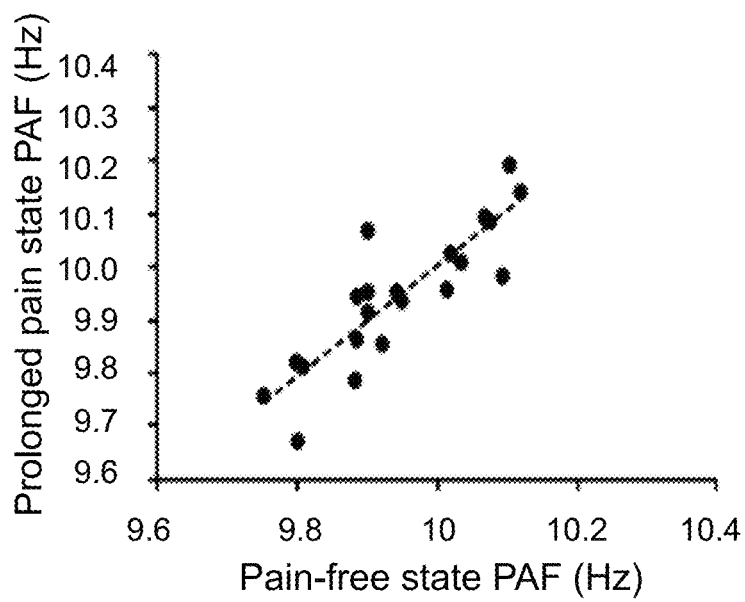
FIG. 3A
FIG. 3B
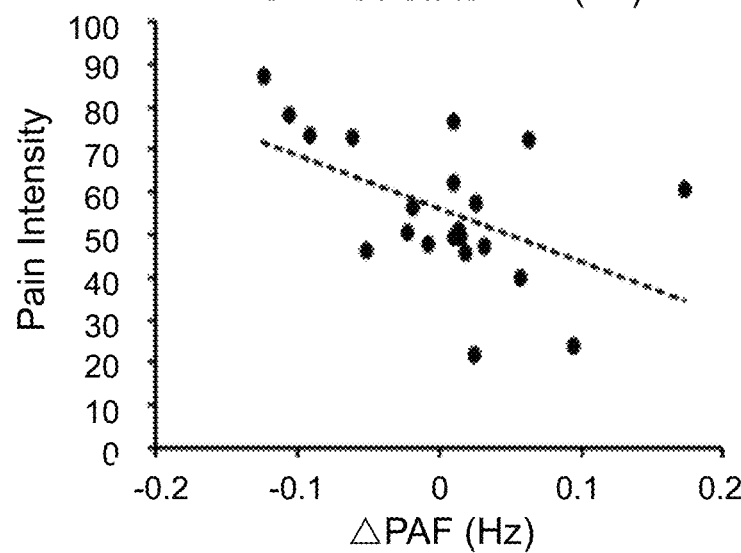
FIG.3C

METHOD FOR PREDICTING PAIN SENSITIVITY

CROSS-REFERENCE TO RELATED APPLICATION

This application is a continuation-in-part of pending International Application No. PCT/US2018/058889, filed Nov. 2, 2018, now abandoned, which claims benefit of priority under 35 U.S.C. § 119(e) of provisional application U.S. Ser. No. 62/580,503, filed Nov. 2, 2017, the entirety of all of which is hereby incorporated by reference.

BACKGROUND OF THE INVENTION

Field of the Invention

The present invention relates generally to the field of medicine and in particular pain assessment and management. More specifically, the present invention provides a simple and rapid method to assess an individual's sensitivity and probability of developing chronic pain using electroencephalography (EEG) alpha wave activity/frequency.

Description of the Related Art

Pain is a salient, multidimensional experience that varies widely between individuals in both intensity and duration. Identifying biomarkers that can determine individual susceptibility for the development of chronic pain is a fundamental step for improved pain treatments.

One approach to this problem has been to investigate the role that neural oscillations like the alpha rhythm play in the individual pain experience (Peng et al., 2015; Ploner et al., 2017). The alpha rhythm represents the predominant oscillatory activity in the EEG which is chiefly observed in primary sensory regions (e.g. vision, auditory). Although previously considered a signature of cortical "idling", significant evidence now suggests that alpha activity plays a top-down role in gating information in sensory cortices depending on task demands (Foxe et al., 1998; Foxe & Snyder, 2011; Jensen & Mazaheri, 2010; Klimesch, 2012, Pfurtscheller et al., 1996). The peak frequency of alpha activity (i.e, the frequency within the 8-12 Hz that has the maximal power) increases from childhood to adulthood and subsequently decreasing with age (Aurlien et al., 2004; Lindsley, 1939, Hashemi et al., 2016; Bazanova & Vernon, 2014). There is evidence that the frequency of alpha activity is positively correlated to measures such as working performance (Klimesch, 1999). More recently, it has been demonstrated that individuals with higher alpha frequencies in the occipital cortex are able to perceive visual information with a finer temporal resolution (Samaha et al., 2015). Peak alpha frequency has been found to be reliable in test-retest studies (Grandy et al., 2013), and appears to be a heritable phenotypic trait (Posthuma et al., 2001; Smit et al., 2006). Taken together, these studies suggest that peak alpha frequency (PAF) could be viewed as a 'state' variable with its subtle fluctuations within an individual reflecting shifts in the excitability of the underlying cortex and its capacity to process information. Alternatively, peak alpha frequency can be viewed as a 'trait' variable with its variability across individuals reflecting cognitive ability.

The variability of alpha frequency has been studied in the context of characterizing disease states in clinical populations, and the subjective experience of pain in the typical population. In patients suffering from central, visceral, and neuropathic pain conditions, peak alpha frequency was slowed relative to matched, healthy controls (Sarnthein et al., 2005; Walton et al., 2010; de Vries et al., 2013, Lim et al., 2016). It has been hypothesized, that the slowing of peak alpha frequency and that the increased power of slower alpha rhythms (8-9.5 Hz) contributes to the generation of pathological pain, perhaps reflecting thalamocortical dysrhythmia (Llinas et al., 2005).

While a number of studies have identified neural signatures that can be used to predict different intensity levels of a noxious stimulus (i.e. high vs low; Iannetti et al., 2005; Wager et al., 2013), peak alpha frequency provides information about individual variability in pain resulting from the same stimulus. Given that pain sensitivity has been identified as a positive predictor of chronic pain development (Hah et al., 2019), this would suggest peak alpha frequency can offer a window into identifying chronic pain risk that was previously inaccessible. Previous research on brain-based markers of chronic pain risk has largely focused on instances where pain is already present (i.e. acute low back pain; Baliki et al., 2012). While useful, such biomarkers may be accessible too late in the transition to chronic pain to allow for full prophylaxis. Unlike these markers, however, peak alpha frequency can be accessed in the pain-free state and could be used by clinicians to intervene prior to injury (e.g. surgery).

In contrast to the slowing of peak alpha frequency associated with chronic pain, exposure to acute, painful stimuli in healthy subjects has been found to increase the frequency of alpha activity (Nir et al. 2010). Furthermore, peak alpha frequency collected from healthy individuals either during or, perhaps more importantly, prior to stimulation were positively correlated with pain intensity (Nir et al., 2010), suggesting that peak alpha frequency reflects processes related to both ongoing pain and individual vulnerability. These findings together suggest a rather complex relationship between types of pain and variations in peak alpha frequency. Transient acute pain increases alpha frequency in the healthy population whereas alpha frequency slows in patients with chronic pain. The slowing of alpha frequency in chronic pain populations could reflect changes in the brain's neural architecture brought about by the constant experience of pain. Supporting this view is a finding that peak alpha frequency had an inverse relationship with duration of chronic pancreatitis (de Vries et al., 2013).

Previous research has consistently observed abnormally slow peak alpha frequency in chronic pain patients (Sarnthein et al., 2005; Walton et al., 2010; Lim et al., 2016), with increasingly slower peak alpha frequency associated with increasingly longer durations of chronic pain (de Vries et al., 2013). This apparent slowing of peak alpha frequency in chronic pain has been interpreted to reflect pathological changes within the brain that occur during the chronification of pain (Llinás et al., 1999). Heightened pain sensitivity is a risk factor for developing chronic pain (Diatchenko et al., 2005), an alternative interpretation of the aforementioned chronic pain findings is that slow peak alpha frequency reflects an increased sensitivity to prolonged pain that predates disease onset. Slow peak alpha frequency may reflect a predisposition for developing chronic pain rather than a result of its development.

The personal experience of pain is highly variable even when the underlying tissue damage is identical. Methods to reliably predict pain intensity is currently lacking. There is, therefore, a recognized need to identify methods that can determine individual susceptibility for developing prolonged pain. Such methods would be beneficial in the clinic since early intervention strategies can be pursued to lower the risk thereby improving pain management. The invention fulfills this longstanding need and desire in the art.

SUMMARY OF THE INVENTION

The present invention is directed to a method for predicting pain sensitivity to prolonged pain in a subject. The method comprises recording a pain-free resting state electroencephalogram of the subject and measuring a pain-free peak alpha frequency from the recorded pain-free EEG. A prolonged pain stimulus is applied to the subject and the subject reports an intensity of pain perceived during the prolonged pain stimulus. The pain-free peak alpha frequency is compared with the reported intensity during the prolonged pain stimulus where the peak alpha frequency correlates negatively with pain sensitivity to the prolonged pain in the subject.

The invention also is directed to a method for predicting a likelihood of increased pain intensity during prolonged pain in a subject. The method comprises recording a pain-free resting state electroencephalogram of the subject and applying a prolonged pain stimulus to the subject. A prolonged pain resting state electroencephalogram of the subject is recorded after an interval of time has elapsed from applying the prolonged pain stimulus. A pain-free peak alpha frequency is measured during the pain-free state and a prolonged pain peak alpha frequency is measured during the prolonged pain state. A shift between the prolonged pain peak alpha frequency and the pain-free peak alpha frequency is calculated to obtain a peak alpha frequency shift ($\Delta$PAF) where the $\Delta$PAF correlates negatively with pain intensity during prolonged pain in the subject.

The invention is directed further to a related method for predicting a likelihood of increased pain intensity during prolonged pain in a subject. The method comprises recording a pain-free resting state electroencephalogram of the subject and applying a prolonged pain stimulus to the subject. A prolonged pain resting state electroencephalogram of the subject is recorded while the prolonged pain stimulus is applied. A pain-free peak alpha frequency is measured during the pain-free state and a prolonged pain peak alpha frequency is measured during the prolonged pain state. A shift between the prolonged pain peak alpha frequency and the pain-free peak alpha frequency is calculated to obtain a peak alpha frequency shift ($\Delta$PAF) where the $\Delta$PAF correlates negatively with pain intensity during prolonged pain in the subject.

The present invention is directed further still to a method for predicting a likelihood of developing chronic pain in a subject after an injury. The method comprises recording an electroencephalogram of the subject during a pain-free state and during a prolonged pain state, measuring the peak alpha frequency from the pain-free state EEG and from the prolonged pain state EEG, and comparing the prolonged pain peak alpha frequency to the pain-free peak alpha frequency, wherein a slower prolonged pain peak alpha frequency compared to the pain-free peak alpha frequency or a difference between the prolonged peak alpha frequency and the pain-free peak alpha frequency shifting toward the pain-free peak alpha frequency indicates that the subject is likely to have chronic pain after the injury. The present invention is directed to a related method for predicting a likelihood of chronic pain in a subject after an injury further comprising, when the subject is likely to have chronic pain, designing a plan to treat the chronic pain.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A shows the method steps used for performing the capsaicin heat pain model in an individual. FIG. 1B shows a representative pain intensity plot generated by using the method shown in FIG. 1A on pain-free, neurotypical adult participants.

FIG. 2A is a top view of a scalp showing the topography of the central alpha wave component from electroencephalography scans averaged across pain group participants. FIG. 2B shows the relationship between the central alpha wave component peak alpha frequency (central peak alpha frequency) and pain intensity recorded during the pain-free state showing that the lower an individual's average peak alpha frequency, the greater their pain. FIG. 2C shows the relationship between the peak alpha frequency and pain intensity recorded during the prolonged pain state showing that the lower an individual's average peak alpha frequency, the greater their pain. FIG. 2D is a comparative analysis of peak alpha frequency in the high pain sensitive group, low pain sensitive group and non-pain control group. The figure shows that the low pain sensitive group displayed the fastest peak alpha frequency across both pain-free and prolonged pain states, the high pain sensitive group displayed the slowest peak alpha frequency across both states, and the control group displayed peak alpha frequency somewhere in between the high and low pain sensitive groups. FIG. 2E is a Bonferroni-corrected pair-wise comparison between high and low pain sensitive groups at various frequencies in the pain-free state showing a significant difference in the alpha wave frequency domain. FIG. 2F is a Bonferroni-corrected pair-wise comparison between high and low pain sensitive groups at various frequencies in the prolonged pain state showing a significant difference in the alpha wave frequency domain.

FIGS. 3A-3C illustrate the relationship between peak alpha frequency shifts ($\Delta$PAF) from pain-free to prolonged pain states and pain intensity. FIG. 3A shows a strong correlation of peak alpha frequency between the pain-free state and the prolonged pain state. FIG. 3B shows the relationship between pain intensity and difference in peak alpha frequency ($\Delta$PAF) between prolonged pain and pain-free states, demonstrating a negatively correlation. FIG. 3C shows the lack of correlation between $\Delta$PAF and peak alpha frequency for the pain-free state, suggesting that pain-free state peak alpha frequency and $\Delta$PAF are distinct elements of pain sensitivity.

FIG. 4A shows a Pearson correlation between observed (actual) pain intensity and predicted pain intensity, which yields a Pearson correlation coefficient (r) of 0.55. FIG. 4B shows that the Pearson correlation coefficient (r)

value for FIG. 4A surpassed the 95th percentile of a null distribution of r values generated (gray line) using permuted peak alpha frequency measures and pain intensity (r=0.22), indicating that the two peak alpha frequency measures can be used to predict pain intensities. The black line indicates the correlation value obtained in the actual leave out approach. FIG. 4C shows a plot of Pearson correlation coefficient (r) versus training set size demonstrating that prediction becomes stable around a training set size of 6 subjects (r=0.49) and increased by a relatively small amount to the maximum training size of 20 (r=0.55), suggesting that the ability to predict future pain intensity from pain-free state peak alpha frequency and ΔPAF is robust and not altered by the cross-validation procedures employed.

FIG. 5A shows data from Phasic heat pain responders. FIG. 5B shows data from Capsaicin Heat Pain responders. FIG. 5C shows data from Capsaicin Heat Pain rekindle responders.

FIG. 6A shows pain-free, sensorimotor peak alpha frequency estimates in Visit 1. FIG. 6B shows Pain-free, sensorimotor PAF and prolonged pain models are stable across Visits.

FIG. 7A shows data from Phasic heat pain responders. FIG. 7B shows data from Capsaicin Heat Pain responders. FIG. 7C shows data from Capsaicin Heat Pain rekindle responders.

FIG. 8A shows data from Phasic heat pain responders. FIG. 8B shows data from Capsaicin Heat Pain responders. FIG. 8C shows data from Capsaicin Heat Pain rekindle responders.

FIG. 9A shows data from Phasic heat pain responders. FIG. 9B shows data from Capsaicin Heat Pain responders. FIG. 9C shows data from Capsaicin Heat Pain rekindle responders.

FIG. 10A shows daily diary pain ratings for Study 1. Asterisks reflect time points where pain was found to be significantly greater than 0 ($\rho<0.05$). FIG. 10B shows Day 0, pain-free sensorimotor peak alpha frequency was negatively correlated with the average pain intensity reported from Days 1-17. The red dotted line reflects the linear regression line of best fit. FIG. 10C shows cohort 1 median split based on the speed of pain-free, sensorimotor peak alpha frequency reveals that "Slow" peak alpha frequency individuals experience greater pain at almost all time points.

FIG. 11A shows mean (+1 standard deviation) of sensorimotor peak alpha frequency estimates at each testing day. FIG. 11B shows study 1 Sensorimotor peak alpha frequency collected at Day 0 is significantly correlated with Sensorimotor peak alpha frequency collected all other time points. Asterisks reflect statistical tests with $\rho<0.05$. FIG. 11C shows shifts in sensorimotor peak alpha frequency (ΔPAF; Average Post-nerve growth factor PAF—Day 0 PAF) are not related to average nerve growth factor pain. The red dotted line reflects the linear regression line of best fit.

FIG. 12A shows a support vector machine trained on Visit 1 pain-free, sensorimotor peak alpha frequency predicts the identity of high and low pain sensitive individuals from the same study at almost all labelling intervals. An F1 score of 1 indicates perfect classifier performance and the dashed red lines reflect the 95th % of a null distribution of F1 scores. FIG. 12B shows a support vector machine trained on Visit 1 pain-free, sensorimotor peak alpha frequency predicts the identity of high pain sensitive individuals from an independent study at all labelling intervals. FIG. 12C shows a support vector machine trained on Visit 1 pain-free, sensorimotor peak alpha frequency predicts the identity of Visit 2 high pain sensitive individuals.

DETAILED DESCRIPTION OF THE INVENTION

Figure 1A:
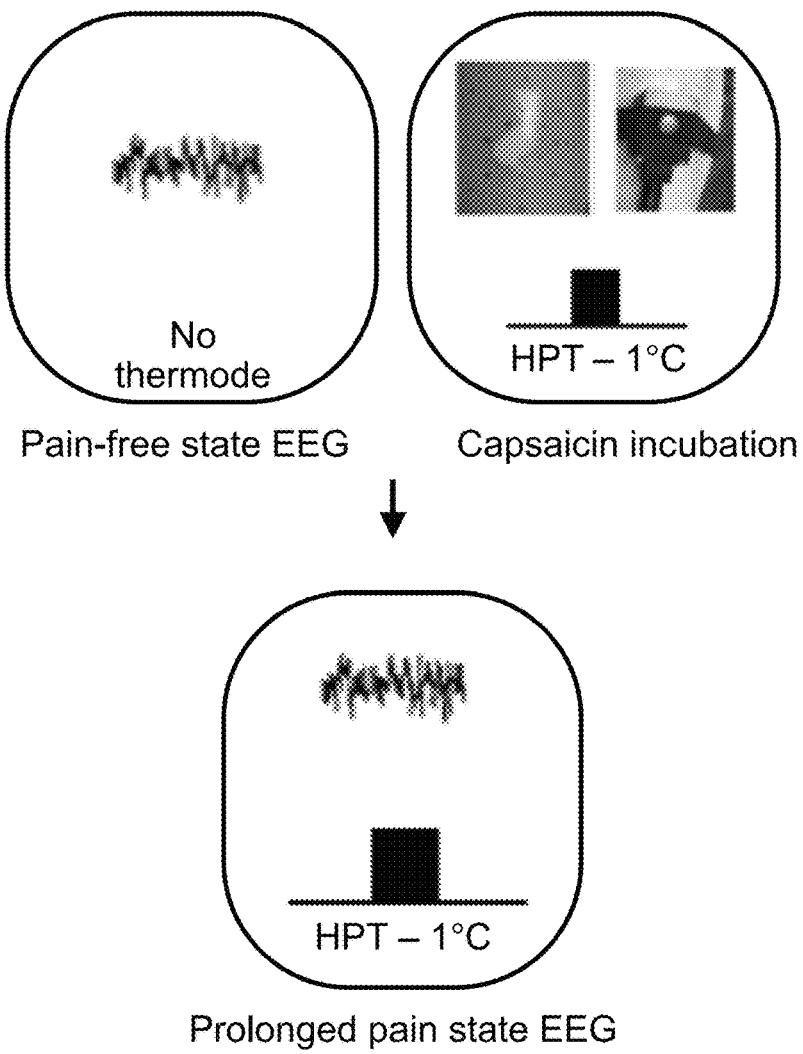
FIGS. 1A-1B illustrate the capsaicin heat pain model.
Figure 1B:
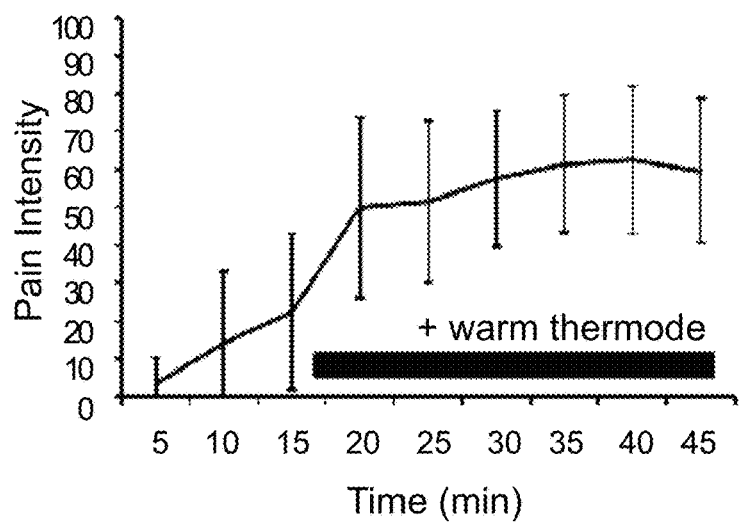

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "injury" refers to expected and unexpected hard and soft tissue damage occurring after a medical procedure, for example, a surgery, or refers to hard and soft tissue damage such as occurs from a bone break or fracture, a sprain, a strain, or a blow resulting in a contusion or refers to the result of overuse of a particular part of the body resulting in, for example, back pain, jaw pain or visceral pain, or a wound or combination of any of these. These examples are non-limiting.

In one embodiment of the invention, there is provided a method for predicting pain sensitivity to prolonged pain in a subject. The method comprises, recording a pain-free resting state electroencephalogram of the subject; measuring a pain-free peak alpha frequency from the recorded pain-free EEG; applying a prolonged pain stimulus to the subject; recording a prolonged pain resting state electroencephalogram of the subject; reporting, by the subject, an intensity of pain perceived during the prolonged pain stimulus; and comparing the pain-free peak alpha frequency with the reported intensity during the prolonged pain stimulus, wherein the peak alpha frequency correlates negatively with pain sensitivity to the prolonged pain in the subject. In this embodiment the pain-free resting state electroencephalogram is recorded from about 45 minutes to about 1 month prior to applying the prolonged pain stimulus.

In this embodiment, the peak alpha frequency is measured at a central alpha wave component at a bandwidth from about 8 Hz to about 14 Hz. For example, the peak alpha frequency may be measured at a central alpha wave component at a bandwidth from 9 Hz to 11 Hz.

In addition, a representative pain stimulus includes but is not limited to a heat stimulus, a cold stimulus, pressure, an electrical stimulus, a punctate stimulus, an ischemia, a muscle pain stimulus or an inflammation, or a combination thereof. The pain stimulus does not cause long-lasting tissue damage. One example of the heat stimulus is heat at a single temperature or capsaicinoid compound in combination with a thermal-contact heat stimulator or a thermode or a combination thereof. One example of the muscle pain stimulus is intramuscular injection of nerve growth factor. In aspects of this embodiment the pain stimulus may be delivered to an arm, a leg, a neck, a face, a viscera, a trunk or a back. For example, the pain stimulus may be delivered to a volar surface on a forearm. One of ordinary skill in this art is able to select a pain stimulus that is suitable for practicing this method and use it under conditions that do not cause tissue damage.

In another embodiment of the present invention, there is provided a method for predicting a likelihood of increased pain intensity during prolonged pain in a subject, comprising the steps of recording a pain-free resting state electroencephalogram of the subject; applying a prolonged pain stimulus to the subject; recording a prolonged pain resting state electroencephalogram of the subject after an interval of time has elapsed from applying the prolonged pain stimulus; measuring a pain-free peak alpha frequency during the pain-free state and a prolonged pain peak alpha frequency during the prolonged pain state; and calculating a shift between the prolonged pain peak alpha frequency and the pain-free peak alpha frequency to obtain a peak alpha frequency shift (ΔPAF), wherein the ΔPAF correlates negatively with pain intensity during prolonged pain in the subject. In this embodiment, recording the prolonged pain encephalogram is performed after the interval of about 15 minutes to about 8 weeks has elapsed.

In this embodiment, the peak alpha frequency is measured at a central alpha wave component at a bandwidth from about 8 Hz to about 14 Hz. For example, the peak alpha frequency may be measured at a central alpha wave component at a bandwidth from 9 Hz to 11 Hz.

In addition, the pain stimulus may be a heat stimulus, a cold stimulus, pressure, an electrical stimulus, a punctate stimulus, an ischemia, a muscle pain stimulus or an inflammation, or a combination thereof. The pain stimulus does not cause long-lasting tissue damage. One example of the heat stimulus is heat at a single temperature, a capsaicinoid compound in combination with a thermal-contact heat stimulator, a thermode or a combination thereof. One example of the muscle pain stimulus is intramuscular injection of Nerve growth factor. In aspects of this embodiment, the pain stimulus may be delivered to an arm, a leg, a neck, a face, a viscera, a trunk or a back. For example, the pain stimulus may be delivered to a volar surface on a forearm. One of ordinary skill in this art is able to select a pain stimulus that is suitable for practicing this method and use it under conditions that do not cause tissue damage.

In a related embodiment, there is provided a method for predicting a likelihood of increased pain intensity during prolonged pain in a subject, comprising the steps of recording pain-free resting state electroencephalogram of the subject; applying a prolonged pain stimulus to the subject; recording a prolonged pain resting state electroencephalogram of the subject while the prolonged pain stimulus is applied; measuring a pain-free peak alpha frequency during the pain-free state and a prolonged pain peak alpha frequency during the prolonged pain state; and calculating a shift between the prolonged pain peak alpha frequency and the pain-free peak alpha frequency to obtain a peak alpha frequency shift (ΔPAF), wherein the ΔPAF correlates negatively with pain intensity during prolonged pain in the subject.

In yet another embodiment of the present invention, there is provided a method for predicting a likelihood of developing chronic pain in a subject after an injury, comprising the steps of recording an electroencephalogram of the subject during a pain-free state and during a prolonged pain state after applying a prolonged pain stimulus to the subject; measuring the peak alpha frequency from the pain-free state EEG and from the prolonged pain state EEG; and comparing the prolonged pain peak alpha frequency to the pain-free peak alpha frequency; wherein a slower prolonged pain peak alpha frequency compared to the pain-free peak alpha frequency or, a difference between the prolonged peak alpha frequency and the pain-free peak alpha frequency shifting toward the pain-free peak alpha frequency indicates that the subject is likely to have chronic pain after the injury. In this embodiment, recording the prolonged pain encephalogram may be performed after the interval of about 15 minutes to about 90 minutes has elapsed.

In this embodiment, the injury may be a result of a medical procedure performed on the subject, may be a wound or may be an experience of pain by the subject. For example, the medical procedure may be a surgery, such as, but not limited to, a back surgery, a muscle surgery or an orofacial surgery. In all embodiments described supra, the subject may include, but is not limited to, an individual who has been recommended for, will undergo or has undergone a medical procedure. For example, the individual may have an injury requiring treatment, will have surgery, has very recently had a surgical intervention, has received a wound or is experiencing the injury as, for example, back pain, jaw pain or visceral pain and/or is being treated for a chronic pain condition. Examples may be, but are not limited to, treatment for chronic back pain, chronic muscle pain or chronic orofacial pain.

In a further embodiment where the subject is likely to have chronic pain, the method comprises designing a plan to treat the chronic pain. In this further embodiment, the plan to treat the chronic pain comprises treating the subject with an analgesic. The analgesic may be an opioid, a non-steroidal anti-inflammatory drug, an aspirin, or a combination thereof. The subject may be treated with analgesics before occurrence of the injury, such as before a medical procedure, or after the medical procedure or other occurrence of the injury or before and continuing after the medical procedure or other occurrence of the injury.

In all embodiments, the peak alpha frequency may be measured at a central alpha wave component at a bandwidth from about 8 Hz to about 14 Hz, for example, 9 Hz to 11 Hz. In all embodiments, the pain stimulus does not cause long-lasting tissue damage and the examples of pain stimuli, for example, heat stimuli and the areas of the subject's body to which the pain stimulus is delivered are described supra.

In addition, in all embodiments, an electroencephalogram may be a scalp EEG, recorded over the sensorimotor cortex region of the brain to obtain a pain-free resting state EEG comprising an alpha wave spectrum component. In one aspect, the electroencephalogram may be recorded in a sitting position with the subject's eyes open. In another aspect of this embodiment, the lights in the room are switched off and the subject in a sitting position is asked to keep the eyes closed prior to recording the EEG.

In the embodiments provided herein the data shows that slow, pain-free peak alpha frequency may reflect a heightened risk for developing chronic pain; that is, slowing of peak alpha frequency in chronic pain may not reflect a result of active disease but instead a heightened pain sensitivity that predates disease onset. Peak alpha frequency reflects the first brain-based biomarker of prolonged pain sensitivity that is available prior to pain onset.

Also provided are the relationship of pain-free peak alpha frequency to two models of prolonged pain, Capsaicin Heat Pain (CHP) and Phasic Heat Pain (PHP), within the same group of participants at two separate timepoints. From these experiments, two key pieces of evidence supporting the hypothesis that pain-free peak alpha frequency is a prolonged pain sensitivity biomarker are presented. First, pain-free peak alpha frequency shares a near identical, negative relationship to Capsaicin Heat Pain and phasic heat pain sensitivity, with increasingly slower peak alpha frequency associated with increasingly greater pain intensity during each test. Reproduction of this relationship across models, despite differences in their length of application, the temperatures used, and the presence of a sensitizing agent, provides important evidence that peak alpha frequency is a marker of prolonged pain sensitivity per se and not specific portions of either model. Preservation of the peak alpha frequency-pain sensitivity relationship through the rekindling phase of the Capsaicin Heat Pain model provides yet another piece of evidence that peak alpha frequency captures an element of the prolonged pain experience that is independent of the local context (i.e. continuous vs. interrupted pain).

Second, the relationship between pain-free, peak alpha frequency and prolonged pain sensitivity is reliable over time. Within the same set of individuals, it is shown that the relationship between pain-free peak alpha frequency and prolonged pain sensitivity is present at two separate testing visits. It should be acknowledged that this relationship was qualitatively stronger at Visit 2, which could be interpreted as evidence that factors that change with repeated testing, such as participant familiarity and/or vigilance, mediate the connection between pain-free peak alpha frequency and prolonged pain sensitivity. While these effects cannot be entirely discounted, a separate explanation centers on the limited participant sample available at Visit 2; restricting Visit 1 analyses to only those participants completing both visits revealed relationship magnitudes, phasic heat pain: $\rho=-0.50$; Capsaicin Heat Pain: $\rho=-0.50$; Capsaicin Heat Pain rekindle: $-0.52$, closer to those found at Visit 2.

This temporally stable association of pain-free peak alpha frequency and prolonged pain sensitivity appears to be a consequence of the temporal stability of the measures themselves. For both pain-free peak alpha frequency and prolonged pain sensitivity, it was found that Visit 1 and Visit 2 estimates were strongly correlated and did not significantly differ from one another. These findings fit well with previous studies of peak alpha frequency and prolonged pain sensitivity that demonstrate each are trait-like measures (e.g. Grandy et al., 2013; Naert et al., 2008; Koenig et al., 2014). Importantly, the average length of time separating visits (~8 weeks), as well as the absence of visual and haptic feedback during rating, provides comfort that the reliability of pain scores is not simply the result of participant's explicit recollection of previous pain. From a broader perspective, these findings suggest the that relationship between pain-free peak alpha frequency and prolonged pain is not uniquely determined at each visit but is instead an association that remains consistent across time; put another way, the same pain-free, peak alpha frequency and the same prolonged pain sensitivity are sampled from individuals at each visit. Indeed, the ability of Visit 1 pain-free peak alpha frequency to predict prolonged pain sensitivity at Visit 2 provides strong evidence in favor of this conclusion. Thus, these findings clearly show that pain-free peak alpha frequency can provide cogent information about prolonged pain sensitivity at both short (i.e. minutes/hours separating peak alpha frequency acquisition and pain testing) and long (weeks/months separating visits) timescales.

Pain-free peak alpha frequency can also predict the identify of high or low pain sensitive individuals. In almost all cases, a support vector machine trained on pain-free peak alpha frequency was able predict the identity of the most pain sensitive individuals. Results suggest that pain-free peak alpha frequency is particularly well suited for identifying high pain sensitive individuals. Importantly, Visit 1 pain-free peak alpha frequency could be used to predict high pain sensitivity at Visit 2 suggesting that pain sensitivity prediction remains relevant across clinically relevant periods of time. Prospective collection of pain-free peak alpha frequency at routine check-ups may therefore prove an effective strategy for ensuring information about an individual's pain sensitivity is available to clinicians in cases of unplanned surgical intervention.

The findings demonstrate that pain-free peak alpha frequency is a reliable predictor of prolonged pain sensitivity. In addition to demonstrating that pain-free peak alpha frequency is related to multiple models of prolonged pain, compelling evidence are provided that this relationship is stable over both immediate, i.e. minutes/hours, and more extended, i.e. weeks/months, periods of time. Furthermore, it is demonstrated that pain-free peak alpha frequency can be used to accurately identify high pain sensitive individuals in multiple datasets. These findings now firmly position pain-free peak alpha frequency as a biomarker of pain sensitivity with untapped potential in clinical settings.

Also provided herein are evidences that pain-free, sensorimotor peak alpha frequency reflects pain sensitivity to a clinically relevant model of musculoskeletal pain. Initial evidence that the presence of pain for more than two weeks is not sufficient to slow peak alpha frequency, suggesting that peak alpha frequency slowing in chronic pain may reflect heightened pain sensitivity that predates disease onset. These results highlight the important role pain-free, sensorimotor peak alpha frequency can play in the clinical identification of those at high risk for developing chronic pain. It is also determined that pain-free, sensorimotor peak alpha frequency could predict the intensity of nerve growth factor pain; increasingly slower pain-free, sensorimotor peak alpha frequency was associated with increasingly greater nerve growth factor pain at multiple time points. More specifically, results demonstrate that pain-free, sensorimotor peak alpha frequency is related to the average, but not the maximum, nerve growth factor pain experienced over a two-and-a-half-week period. This suggests that peak alpha frequency provides relevant information about the entire time course of pain. In line with this interpretation, the median split analysis demonstrated that Slow peak alpha frequency individuals experience greater pain than Fast peak alpha frequency individuals at almost all post-nerve growth factor time points.

The consistent association between pain sensitivity and peak alpha frequency across EEG channels likely suggests that cognitive processes linked to widespread cortical networks, such as attention, play an important role in mediating this relationship. Processes such as top-down attention seem well-positioned to impact pain sensitivity given that self-reported attention to pain is a strong predictor of pain sensitivity (Baum et al., 2011) and directing attention away from pain and towards a cognitive task can reduce pain perception and pain-related brain activity (Malloy & Milling, 2010; Seminowicz et al., 2004). Along similar lines, factors that affect both attentional control and pain sensitivity, such as sleep quantity (Lim & Dinges, 2008; Onen et al., 2001), may be useful in understanding how individual differences in peak alpha frequency arise in the first place. Ultimately, use of multi-modal imaging, like simultaneous EEG-fMRI, alongside relevant questionnaires will be needed to resolve the identity of the peak alpha frequency-related processes involved in determining pain sensitivity.

The instant application also provides important evidence that peak alpha frequency's relationship to pain extends to musculoskeletal pain and, perhaps more importantly, to a duration of pain (weeks) that far exceed the length of tests in minutes/hours. This provides important evidence that peak alpha frequency has real potential for predicting pain sensitivity to noxious events that occur over clinically relevant timescales. Post-surgical pain at these timescales has been shown to be relevant for determining chronic pain vulnerability (e.g. Katz et al., 1996), with one recent study demonstrating a strong, positive association between the magnitude of pain reported over the 10 days immediately following invasive surgery and pain persistence (Ha et al., 2019). Furthermore, the collection of pain ratings outside of the lab (i.e. by electronic diary) provides the best evidence to date that peak alpha frequency can reflect real world pain and is not confounded by factors associated with laboratory collection of pain ratings (i.e. participant alertness). It is also notable that an upcoming TMS intervention in Study 2, which could have affected pain ratings through expectation of analgesia (Goffaux et al., 2009), did not appear to impact the relationship between peak alpha frequency and nerve growth factor pain. Investigating if and how participant expectation impacts the peak alpha frequency-pain sensitivity relationship is an important future direction as expectations appear to play a critical role in the variability of clinical pain outcomes (e.g. Kalaukalani et al 2001).

It is also demonstrated that sensorimotor peak alpha frequency slowing does not necessarily occur as a result of a long-lasting pain experience. Sensorimotor peak alpha frequency remained stable over a 14-day period despite the presence of ongoing nerve growth factor pain. Participants were just as likely to experience increases or decreases in peak alpha frequency speed after nerve growth factor injection.

The present invention thus provides a number of advantages and uses, which are described below, however, the advantages and uses are not limited by this description. Embodiments of the invention are better illustrated with reference to the Figure(s), however, such reference is not meant to limit the invention in any fashion. The embodiments and variations described in detail herein are to be interpreted by the appended claims and equivalents thereof Example 1

Methods and Methodology
Participants

Study A: Forty-four pain-free, neurotypical adult participants mean age=28.4 years, age range=19 to 42 years) were recruited for the experiment. Twenty-seven (27) of these participants were randomly assigned to the Pain group that would be administered topical capsaicin. Seventeen (17) participants were assigned to the Non-Pain group, which would not be administered topical capsaicin. The Non-Pain group served to control for effects of ongoing stimulation and attention and further, to confirm that prolonged pain sensation was a result of the capsaicin application and not just the warm thermode. More participants were assigned to the capsaicin group to account for the variability in response to topical capsaicin (Liu et al., 1998).

Study B: Sixty-one pain-free, adult participants (31 males, mean age=27.82, age range=21-42) without history of neurological or psychiatric disorder took part in the experiment. This study was approved by the University of Maryland, Baltimore Institutional Review Board, and informed written consent was obtained from each participant prior to any study procedures. The study was pre-registered on ClinicalTrials.gov (NCT02796625).

Study C: Thirty-one healthy, right-handed individuals participated. Twenty individuals participated in Study 1 (11 male, mean age=23.20, S.D.=4.30) and eleven individuals participated in Study 2 (5 male, mean age=24.30, S.D.=6.90). Handedness was assessed using the Edinburgh handedness questionnaire (Oldfield, 1971). Participants with a history of neurological, psychiatric, musculoskeletal or upper limb conditions were excluded and a transcranial magnetic stimulation (TMS) safety screen was completed prior to study enrollment (Keel et al., 2001). All participants provided written informed consent consistent with the Declaration of Helsinki. Experimental procedures were approved by the institutional ethics committee (H10184) at Western Sydney University.

Electroencephalography

Scalp Electroencephalography (EEG) was collected from an EEG cap housing a 64 channel Brain Vision actiCAP system (Brain Products GmbH, Munich, Germany) labeled in accord with an extended international 10-20 system (Oostenveld and Praamstra, 2001). All electrodes were referenced online to an electrode placed on the right earlobe and a common ground set at the FpZ site. Electrode impendences were maintained below 5 k$\Omega$ throughout the experiment. Brain activity was continuously recorded within 0.01 to 100 Hz bandpass filter, and with a digital sampling rate of 500 Hz to 1000 Hz. The EEG signal was amplified and digitized using a BrainAmp DC amplifier (Brain Products GmbH, Munich, Germany) linked to Brain Vision Recorder software (version 2.1, Brain Products GmbH, Munich, Germany).

For study C EEG data was recorded continuously DC-70 Hz from 19 scalp sites (Fp1, Fp2, F3, Fz, F4, F7, F8, C3, Cz, C4, P3, Pz, P4, P7, P8, T7, T8, O1, and O2) and M2 with an electrode cap using sintered Ag/AgCl electrodes. M1 was used as the active reference and the cap was grounded by an electrode located between AF3 and AF4. Electro-oculogram (EOG) was recorded using sintered Ag/AgCl electrodes placed 2 cm above and below the left eye for vertical movements, and on the outer canthus of each eye for horizontal movements. Data were acquired at 1000 Hz from DC–70 Hz with the default gain setting and a 50 Hz notch filter using a Neuroscan Synamps 2 digital signal-processing system and Neuroscan 4.3.1 Acquire software. Impedances were <5 k$\Omega$ for cap, EOG, and reference electrodes.

Thermal Stimulator and Pain Scale

Thermal stimuli were delivered to the volar surface of the participant's left forearm using a thermal contact heat stimulator (27 mm diameter Medoc Pathway CHEPS Peltier device; Medoc Advanced Medical Systems Ltd., Ramat Yishai, Israel). Unless otherwise stated, pain ratings were collected continuously with a manual analog scale consisting of a physical sliding tab (Medoc Advanced Medical Systems Ltd., Ramat Yishai, Israel). Prior to testing, participants were instructed that the lower and upper bounds of the scale represented no pain and the most pain imaginable, respectively, and that they should continuously update the position slider to indicate the amount of pain currently being experienced. Care was taken by experimenters to avoid providing numerical anchors when describing the scale and no additional physical landmarks were present on the scale. Prior studies have found that analog scales are superior to numerical scales for capturing the pain power function often encountered in psychophysical testing (Price et al., 1994; Nielsen et al., 2005). Prior to testing, participants were given an opportunity to practice using the device with their eyes open and closed. During testing, participants were permitted to briefly open their eyes while rating. Pain ratings were collected from the manual analog scale at a rate of 1000 Hz. Manual analog scale data was transformed by converting the horizontal position of the slider into a continuous value between 0 and 100.

Quantitative Sensory Testing

Participants were asked to complete four threshold tests: 1) to report when they felt a temperature increase (Warmth Detection Threshold); (2) to report when they felt a temperature decrease (Cool Detection Threshold); (3) to report when an increasing temperature first became painful (Heat Pain Threshold); and (4) to report when a decreasing temperature first became painful (Cold Pain Threshold).

A total of three trials were presented for each test with an ISI of 4-6 seconds (randomly determined on a per trial basis). Participants provided feedback for each test by clicking either the left or right button of a computer mouse placed in their right hand. For each test, temperatures were applied with a rise rate of 1° C./second and return rate of 2° C./second (initiated on any mouse click).

All testing was performed on the volar surface of the left forearm. The distance from the wrist to elbow joint was measured and the forearm was divided into three equal length zones. For each test, the first trial was administered to the zone closest to the wrist, the second trial administered to the middle forearm zone, and the third trial administered to the zone closest to the elbow.

Phasic Heat Pain (PHP) Model

Temperatures used during the Phasic Heat Pain model were determined during each participant's initial screening visit to the laboratory (Visit 0). During these sessions, participants were exposed to 12, 20 second trials in which a single temperature (2.5 second rise and fall) was applied to the volar surface of the left forearm. At the conclusion of each trial, participants reported the average pain they experienced during temperature application; participants were instructed to report pain ratings on a scale of 0-10, with 0 indicating no pain and 10 the most pain imaginable. This was the only time during the experiment at which participants were asked to rate along a numerical pain scale. Temperatures ranged from 37 to 48° C. (intervals of 2° C., starting as if 37° C. was 38° C.) and each temperature was presented twice in a pseudorandom order. Trials were separated by 10 seconds and after each trial the thermode was moved to a neighboring forearm zone in order to minimize sensitization. Using pain reports from these trials, the temperature that most closely evoked an average pain rating of $5/10$ was selected. This level of pain was targeted in order to best match the intensity of pain evoked by the Capsaicin Heat Pain model (Furman et al., 2018). For a few participants, none of applied temperatures were able to produce a pain rating close to $5/10$. For these individuals, 48° C. was used during Phasic Heat Pain testing.

The Phasic Heat Pain model itself consisted of a series of five consecutive stimulus trains. Each train lasted one minute and consisted of application of a predetermined temperature for 40 seconds (rise and fall times of 2 s) followed by application of a neutral skin temperature stimulus (32° C.) for 20 seconds. Phasic Heat Pain scores were calculated by averaging pain ratings from the five, forty second periods in which the temperature was present.

Prolonged Pain Induced by the Capsaicin-Heat Pain Model

Thermal stimuli were delivered to the volar surface of participant's left forearm using a thermal-contact heat stimulator (30×30 mm Medoc Pathway ATS Peltier device; Medoc Advanced Medical Systems Ltd., Ramat Yishai, Israel). Prior to the beginning of the experiment all participants underwent a brief sensory testing session in which they were asked to report when they felt a change in temperature (for warmth detection threshold (WDT)) or when the temperature first became painful (heat pain threshold (HPT)). For warmth detection threshold and heat pain threshold three and four trials were presented respectively, and the average across trials, rounded down to the nearest integer.

Prolonged pain was modelled following a procedure modified from previous studies (Anderson et al., 2002). About 1 g of 10% capsaicin paste (Professional Arts Pharmacy, Baltimore, Md.) was applied topically to the volar surface of the left forearm, fixing it in place with a Tegaderm™ bandage. After 15 minutes of exposure, the thermode was placed over the top of the Tegaderm bandage at a temperature that was greater than the warmth detection threshold and at least 1° C. below the heat pain threshold, in general the thermode temperature was held at 40° C. for all participants. This configuration is termed the capsaicin-heat pain model (C-HP). To ensure that capsaicin produced a stable, long-lasting pain, participants were asked to provide pain intensity ratings every minute for the first five minutes following thermode placement. The thermode temperature was adjusted during this time to achieve a consistent pain intensity above 20 on a 0-100 point scale, lowering the temperature if the pain was intolerable or, increasing the temperature closer to the heat pain threshold is no pain was perceived. Once the five minute period elapsed, the temperature was held in place for 25 minutes and the participants asked to rate pain intensity every 5 minutes.

This temperature was selected because, in the absence of capsaicin, most individuals find it non-painful thereby providing comfort that any pain generated by this temperature during capsaicin exposure is likely a consequence of the agent's sensitizing effects. Capsaicin Heat Pain scores were calculated by averaging ratings across the entire five-minute Capsaicin Heat Pain test that followed incubation.

To further test of the reliability of Capsaicin Heat Pain sensitivity, a "rekindling" phase (Capsaicin Heat Pain rekindle; Dirks et al., 2003) was included. After the initial Capsaicin Heat Pain testing was completed, an icepack (see below for details) was applied to the forearm until a complete termination of pain was reported. Afterwards, the thermode was again placed over top of the site of capsaicin application, heated to 40° C., and held in place for five minutes. Capsaicin Heat Pain rekindle scores were calculated as the average of the pain ratings provided during this five-minute period.

This procedure does not cause lasting tissue damage. Previous studies showed that topical capsaicin evoked no pain or hypersensitivity in some participants. Participants who did not develop moderate pain, set at a reported pain intensity level of 20 (details of the scale provided below) were excluded from the study.

Icepack Application

At the conclusion of the Phasic Heat Pain and Capsaicin Heat Pain tests, the thermode was removed and a disposable icepack was applied the stimulated area of the left forearm. This was done to prevent pain carryover from one test to another and to ensure that pain ratings for subsequent tests were captured from a starting state of no ongoing pain. The icepack was left in place until the complete absence of pain was reported by the participant. No participants indicated that the icepack itself was ever painful. Following each icepack application, a 5-minute pain-free, eyes closed EEG session occurred.

Nerve Growth Factor-Induced Muscle Pain

Nerve growth factor is an endogenous neuromodulator that is essential for the development and maintenance of the nervous system (Lewin et al., 1992). Intramuscular injection of Nerve growth factor in humans has been shown to induce progressively developing, muscle pain that is sustained for up to 21 days and is accompanied by hyperalgesia, movement-evoked pain and reduced function (Bergin et al., 2015). After cleaning the skin with alcohol, a dose of 5 µg (0.2 ml) sterile, recombinant human Nerve growth factor was given as a bolus injection in the ECRB muscle belly with a 1 ml syringe using a 27 G disposable needle (Schabrun et al., 2016).

Procedures

Study A: A summary of the order of procedures is described in FIG. 1A.

Pain-Free Resting State EEG:

Participants were seated in a comfortable chair and underwent a brief sensory testing session to establish their individual capsaicin-heat pain threshold. Participants rate their current pain intensity every five minutes on a 0-100 scale, with the anchors 0, not at all painful and 100, most intense pain imaginable. In total, participants provided six pain intensity ratings during this testing session. Ratings were always given during a resting period. At the conclusion of this testing session and immediately following the final pain intensity rating, all lights in the testing room were turned off and participants were instructed to close their eyes, remain still, and relax without falling asleep. Continuous EEG was recorded during this pain-free resting state for three minutes in both the Pain and Non-Pain groups.

Prolonged Pain Resting State EEG:

At the completion of the pain-free state EEG recording, the lights in the testing room were turned on, capsaicin was applied to the participant's left forearm, as described above, and the thermode was placed directly on top of the capsaicin application. During this incubation period participants were instructed to relax without falling asleep. The thermode was kept at 32° C., and participants were asked to provide a pain intensity rating every three minutes over a total of fifteen minutes. For participants in the Non-Pain group, the thermode was placed as above, though the capsaicin application step was omitted. Following this incubation period, the thermode temperature was increased to a warm temperature 3° C. below the previously determined HPT. Participants were asked to provide a pain intensity rating at 1-minute intervals for five minutes. If the participant did not report feeling any sensation from the capsaicin, the temperature was increased in 1° C. increments, ensuring that the final testing temperature is at least 1° C. below the established HPT. For Non-Pain group participants, adjustments were only made to lower the temperature if pain was reported. After the five-minute period has elapsed, participants were instructed to perform the cognitive task described in the earlier section for twenty-five minutes to obtain a total of 6 pain intensity ratings. Immediately after the last rating was provided, a three minute "stimulation" resting state EEG was collected. For the Pain group, this "prolonged pain" resting state was collected with the capsaicin and warm thermode placed on the forearm. For the Non-Pain Group, the resting state was collected with the warm thermode placed on the forearm without capsaicin.

Study B: In order to allow sufficient time for any long-term effects of capsaicin exposure to subside, visits were separated by 21 days or more (except for one case where a subject returned at 19 days because of a scheduling conflict; mean separation of Visit 1 and Visit 2=54.74 days, S.D.=55.92 days, range=19-310 days).

Participants first underwent an initial screening visit, Visit 0, that included quantitative sensory testing as well as additional tests to ensure that 40° C. was rated as minimally-painful, to identify the appropriate phasic heat pain temperature, and to provide initial exposure to capsaicin. For the first four participants, these procedures, excluding capsaicin exposure, were performed during Visit 1.

Participants returned for Visit 1 at least three weeks after completing Visit 0. Most participants then returned at least three weeks after Visit 1 for Visit 2. Procedures for Visits 1 and 2 were identical. For the entirety of Visits 1 and 2, participants were seated in a comfortable chair in a quiet room that was isolated from strong electrical interference. For all EEG sessions, lights in the testing room were turned off and participants were instructed to close their eyes, remain still, relax without falling asleep, and continuously rate any pain they experienced with the manual analog scale placed at their right hand. Visits 1 and 2 began with quantitative sensory testing. For the first four participants, this sensory testing was not performed at Visit 2. After quantitative sensory testing, a brief 2-minute EEG was collected to ensure the quality of EEG recording. Next, a room temperature thermode was placed onto the left forearm while eyes closed, pain-free EEG was collected for 5 minutes. The primary objective of the current study was to use peak alpha frequency recorded during this pain-free period as a predictor of subsequent pain sensitivity during Capsaicin Heat Pain and phasic heat pain.

Following the pain-free EEG, prolonged pain was induced with the phasic heat pain model. During the five minutes of phasic heat pain, EEG was collected while participants rested with their eyes closed and continuously rated the intensity of any perceived pain. Upon completion of the phasic heat pain model, a disposable ice pack was placed onto the participant's left forearm until they reported being completely free of pain after which 5 minutes of eyes closed EEG was collected. Next, the second model of prolonged pain, Capsaicin Heat Pain, was induced. Participants were instructed to continuously rate the intensity of experienced pain during this incubation period.

Following the 20-minute incubation period, and with the thermode temperature still held at 40° C., 5 minutes of eyes closed, continuous EEG was recorded while participants continuously rated the intensity of any perceived pain. An icepack was then applied to the forearm and, once pain was reported to be completely absent, 5 minutes of eyes closed EEG was collected. Afterwards, a 40° C. thermode was placed over the site of capsaicin application to induce Capsaicin Heat Pain rekindling. Five minutes of eyes closed EEG was then recorded while participants continuously rated the intensity of any perceived pain.

Study C:

Available data from two studies involving the same pain model and resting state EEG acquired at baseline.

Study 1. Participants visited the laboratory on 5 occasions: Days 0, 2, 4, 6, and 14. Day 0 outcome measures included eyes closed resting state EEG, pressure pain thresholds, transcranial magnetic stimulation (TMS)-derived motor cortical maps, and a number of questionnaires related to affect and pain (i.e., Pain Catastrophizing Scale; Sullivan et al., 1995); data regarding transcranial magnetic stimulation maps and questionnaires will be reported elsewhere. The time of the day in which testing occurred varied between subjects but was held constant within subject across the study. EEG recordings lasted a total of three minutes, during which participants were instructed to sit quietly with their eyes closed. EEG, Pressure pain thresholds, and motor cortical maps were also collected at the beginning of visits occurring on Days 2, 4, 6, and 14. Nerve growth factor (NGF) was injected into the belly of the right extensor carpi radialis brevis (ECRB) muscle immediately following the collection of outcome measures on Days 0, 2, and 4. Electronic pain diaries (described below) were administered on each alternative day from Day 1 to Day 21.

Study 2. Participants visited the laboratory on 3 occasions: Days 0, 2, and 4. Collected outcome measures were identical to those performed on Days 0, 2, and 4 in Study 1 except EEG (3 minutes of eyes closed resting state) was only collected on Day 0. Nerve growth factor was injected into the belly of the right ECRB immediately following collection of all outcome measures on Days 0 and 2. Electronic pain diaries were administered on Days 0, 2, and 4. The length of Study 2 was shortened due to the presence of an intervention occurring after Day 4. After day 4, a repetitive transcranial magnetic stimulation (primary motor cortex, 10 Hz, 1200 stimuli) intervention was applied for 5 consecutive days to modulate pain.

While studies 1 and 2 differed in their protocols, the relationship between pain-free peak alpha frequency and nerve growth factor pain sensitivity were stable regardless of these differences.

Electronic Pain Diary

Pain was assessed using an 11-point numerical rating scale anchored with 'no pain' at 0 and 'worst imaginable pain' at 10. Pain diary information was collected through an internet website. Participants were given midday reminders to complete diaries and were allowed to submit ratings at any time on the queried day.

Data Processing

Study A: The primary data of interest were the resting state EEGs acquired prior to and during prolonged capsaicin pain in the same subject ("within-subject"). Pre-processing of EEG data was done using EEGLAB 13.6.5b (Delorme and Makeig, 2004) using an approach similar to that used previously (Scheeringa et al., 2011a; Scheeringa et al., 2011b). Here, the first step involved band-pass filtering the EEG between 5 and 16 Hz using the function 'eegnewfilt' after which Infomax (extended) independent component analysis (ICA) was performed (Bell and Sejnowski, 1995). It should be noted that the ICA was performed on resting state EEG data combined across the pain-free and prolonged pain states. The obtained unmixing matrix was applied to the unfiltered data resulting in components that retained broadband spectral content. A Fourier transform was performed on the time series of each component to obtain a frequency-power spectrum for each component. The frequency-spectra of the components was visually inspected for each participant to identify components that had a clear alpha peak (8-14 Hz) and a scalp topography suggesting the source predominately over the sensorimotor cortices (the "central component").

Study B: Because the primary objective was predicting pain sensitivity, the EEG data of interest were the initial pain-free EEGs collected at the beginnings of Visits 1 and 2. Preprocessing began with filtering the data between 0.2 and 100 Hz using a linear FIR filter. Channel data were then visually inspected and overtly noisy channels were removed from further analysis. Removed channels were not interpolated. On average, 1.64 (S.D.=1.92, range: 0-8) and 1.79 (S.D.=1.79, range: 0-6) channels were removed per individual from Visit 1 and Visit 2 datasets, respectively. Finally, Principal Components Analysis (PCA) was performed and components with spatial topographies and time series resembling blinks and/or saccades were removed from the data.

Channel level data was used to increase the ease with which methods can be reproduced. Although it may decrease the signal to noise ratio of the data, this approach eliminates the need to identify ICA components on a participant by participant basis and is equally effective for capturing the peak alpha frequency-pain sensitivity relationship (Furman et al., 2019). For channel level analyses, focus was on channels (C3, Cz, and C4) that most strongly reflected the sensorimotor component topography observed (Furman et al., 2018). If a channel from this sensorimotor region of interest (ROI) was removed due to noise, only the remaining channels were used; this affected few participants (Visit 1: n=4; Visit 2: n=1) and no participant had more than one channel removed. In order to make the current results easily comparable to previous findings, all main analyses use peak alpha frequency calculated from this sensorimotor ROI; use of this ROI is not intended to imply a mechanism or source for any documented effects. To explore if additional EEG channels capture the peak alpha frequency-pain sensitivity relationship, the surface Laplacian was computed following preprocessing (Perrin et al., 1989).

Study C: The EEG data of interest was the resting state EEG sessions collected at the beginning of Day 0, 2, 4, 6, and 14 in Study 1 and at the beginning of Day 0 in Study 2. EEG collected at Day 0 represents a pain-free estimate of activity. Initial processing of EEG data was performed using EEGLAB 13.6.5b (Delorme and Makeig, 2004). Processing began by downsampling the data to 500 Hz and filtering between 2 and 100 Hz using a linear FIR bandpass filter. Principal Components Analysis (PCA) was performed and components with spatial topographies and time series resembling blinks and/or saccades were removed from the data. Channel data were then visually inspected and overtly noisy channels were removed from further analysis. Removed channels were not interpolated. On average, very few channels were removed per subject, 0.52 (range: 0-3), 0.30 (range: 0-2), 0.45 (range: 0-2), 0.15 (range: 0-1), and 0.25 (range: 0-2) channels removed for Day 0, 2, 4, 6 and 14 datasets, respectively. Data from remaining channels were re-referenced to the common average reference (i.e., mean across all remaining channels).

For channel level analyses, focus was on channels that most strongly contributed to the sensorimotor component from the first study on sensorimotor peak alpha frequency (Furman et al., 2018). Thus, the sensorimotor region of interest (ROI) included only the C3, Cz, and C4 channels. Across all datasets, no participant had one of these three channels rejected due to noise.

Quantification of Peak Alpha Frequency

The frequency decomposition of the central component data was done using the routines in FieldTrip as discussed by Oostenveld and colleagues (Oostenveld et al., 2011). The data was segmented into 5-second epochs and power spectral density in the 2-40 Hz range was derived for each epoch in 0.2 Hz bins using the 'ft_freqanalysis_mtmfft' function. A Hanning taper was applied to the data prior to calculating the spectra to reduce any edge artifacts (Mazaheri et al., 2010; Mazaheri et al., 2009; Mazaheri 2014). The peak alpha frequency for each 5-second epoch was calculated using a center of gravity (CoG) method as described (Jann et al., 2012; Jann et al., 2010; Klimesch, Schimke, & Pfurtscheller, 1993; Brotzner et al., 2014; Klimesch, 1999), where CoG is defined by the relationship;

$$CoG = \frac{\sum_{i=1}^{n} f_i * a_i}{\sum_{i=1}^{n} a_i}$$

where $f_i$ is the $i^{th}$ frequency bin including and above 9 Hz, n is the number of frequency bins between 9 and 11 Hz, and $a_i$ is the spectral amplitude for $f_i$. peak alpha frequency, as well as power at the peak alpha frequency bin (peak alpha frequency Power) were calculated for the central alpha components for every 5-second epoch and then averaged. peak alpha frequency was calculated from the frequency spectra of each 5-second epoch and average it, rather than use the averaged power spectra (that is, spectra of the 5-second epoch average). This is because the latter method would bias the peak alpha frequency to trials with high amplitude activity. Given that peak frequency is being estimated on an epoch-by-epoch basis, the CoG approach was selected since this would be appropriate when multiple peaks are detected in the alpha range, thereby avoiding errors due to spurious noise. The CoG approach looks at an overall shift in the mass of a bandwidth, rather than a single peak (Brotzner et al., 2014; Klimesch, 1999).

For calculations of CoG, a narrow band width between 9-11 Hz was used rather than the broad, 8-14 Hz bandwidth attributed to the alpha wave component in EEG. This is to minimize fluctuations in pink noise (1/f) contributing to errors in calculated peak alpha frequency values. Using simulations, it was determined that the 9-11 Hz bandwidth is more robust to increases in pink noise compared to the 8-14 Hz bandwidth.

Statistical Analysis

Study A: An independent samples t-test was used to investigate whether capsaicin led to heightened pain intensity. Average pain intensity ratings to capsaicin were determined for each participant by averaging the six ratings during the prolonged pain state. Average pain intensity ratings were compared between Pain and Non-Pain groups using an independent samples t-test. This test was performed separately for the whole sample and the sample that excluded subjects in the Non-Pain group who developed pain and subjects in the Pain group who had <20/100 pain.

In order to investigate if central component peak alpha frequency values during pain-free and prolonged pain states were related to pain intensity, each Pain group participant's central component peak alpha frequency during the pain-free state (that is, before the administration of capsaicin) and during the prolonged pain state were correlated with their averaged pain intensity. To account for the possibility that the relationship between peak alpha frequency and pain intensity ratings could be confounded by the temperature of the thermal device, a partial correlation was performed between peak alpha frequency and pain, controlling for thermode temperature.

For all correlational analyses, Pearson's correlation coefficients were used to test the relationship between variables. Analyses were also conducted using Spearman's rank order correlations, which yielded similar results. As an additional test to investigate whether alpha wave frequency was related to pain sensitivity, the Pain group participants were separated into "high" and "low" pain sensitive groups by performing a median split based on pain intensity. A 2×2 Repeated Measures ANOVA with group (high pain sensitive vs low pain sensitive vs Non-Pain)×state (pain-free vs prolonged pain state) serving as between-subject (different subjects) and within-subject (same subject) factors respectively was used to assess how central alpha wave component peak alpha frequency differed amongst groups and how it changes in response to C-HP. Next, a determination was made whether changes in central alpha wave component peak alpha frequency from baseline to prolonged pain state are related to the pain intensity reported by the participants. This peak alpha frequency shift (ΔPAF) was calculated by subtracting pain-free state peak alpha frequency from the prolonged pain state peak alpha frequency. The ΔPAF was then correlated with pain intensity a partial correlation was performed to control for the impact of thermode temperature. Hierarchical multiple regression was used to test the independent contributions of baseline resting state peak alpha frequency and ΔPAF. In this model, pain intensity was the dependent variable and baseline resting state peak alpha frequency and ΔPAF were the independent variables entered sequentially in the model.

A leave-one-out regression was also performed to formally evaluate the ability of baseline peak alpha frequency and ΔPAF to predict Capsaicin heat pain model sensitivity. This was achieved by generating a series of regression models using baseline central component peak alpha frequency and central component ΔPAF from all but one Pain group individual. The resulting model intercept and unstandardized beta coefficients were used to generate a pain prediction for any single individual withheld from model building. This procedure was repeated iteratively so that each individual served as the test participant for exactly one regression model. The accuracy of these pain predictions was then tested by calculating the Pearson correlation between actual pain intensity and the pain intensity predicted by the leave-one-out models. To test the significance of this prediction, the aforementioned procedure was repeated 10,000 times using randomly shuffled pain and peak alpha frequency measures to bootstrap a null distribution of r values. The 95% of the null distribution was used as a significance cutoff for assessing the predictive ability of peak alpha frequency and ΔPAF. To ensure that results generalized beyond this maximally sized training set, the above analysis was repeated with training set sizes ranging from 3 individuals to 19 individuals. For each training set size, a separate regression model was generated for each possible unique combination of a given training size and the overall correlation between all predictions and observed pain intensity was assessed with a Pearson correlation.

Study B: All analyses were performed using custom scripts implemented in the Matlab environment (version R2013A). Statistical tests were conducted in Matlab or SPSS (Version 25).

Previous work has found that Capsaicin Heat Pain evokes limited pain or hypersensitivity in roughly one third of individuals (Liu et al., 1998, Walls et al., 2017). While the reasons for this remain unclear, certain physiological factors, such as genetic polymorphisms (Campbell et al., 2009), appear to play a role in limiting the effects of the TRPV1 agonist itself. For this reason, it is difficult to determine whether insensitivity to capsaicin reflects a failure of the Capsaicin Heat Pain model or an individual's sensitivity to pain. To address this problem, participants were separated into three pain response classes: 1) individuals who display a clear pain response to Capsaicin Heat Pain (average pain>=10/100) at either Visit 1 or Visit 2 (Capsaicin Heat Pain responde"); 2) individuals who display a clear pain response to phasic heat pain at either Visit 1 or Visit 2 but no response to Capsaicin Heat Pain at either visit (average pain<10/100; Capsaicin Heat Pain non-responder); and 3) individuals who do not display a clear pain response to phasic heat pain or Capsaicin Heat Pain at either visit high tolerance). For the high tolerance pain class, the presence of phasic heat pain insensitivity provides important evidence that Capsaicin Heat Pain insensitivity is unlikely to reflect model failure alone. To ensure that results were not confounded by variability associated with an individual's physiological ability to experience Capsaicin Heat Pain, main analyses was focused on Capsaicin Heat Pain responder and high tolerance individuals. For all tests involving phasic heat pain, results when including all three pain classes are also provided.

To determine if sensitivity to prolonged pain is similar across prolonged pain models, a series of pairwise correlations was calculated between all possible test pairs at each visit. For these and all other correlational analyses, Spearman's rank order correlations were computed, and outliers were defined as data points greater than 2.5 standard deviations above or below the mean value obtained from Visit 1 data. To account for multiple correlations between prolonged pain tests, Bonferroni corrections were applied at the visit level yielding a corrected significance threshold of $\rho=0.0167$. It was also assessed whether sensitivity is reliable across prolonged pain tests using Cronbach's α.

To begin testing whether pain-free, sensorimotor peak alpha frequency is related to prolonged pain sensitivity, a series of pairwise correlations was performed between pain-free, sensorimotor peak alpha frequency and each pain test (phasic heat pain, Capsaicin Heat Pain, and Capsaicin Heat Pain rekindle) at each visit. Bonferonni corrections were applied to correlations between peak alpha frequency and prolonged pain tests for each visit (3 tests) yielding a corrected significance threshold of $\rho=0.0167$. For each test, it was also investigated the effect of sex by performing correlations separately for males and females. To ensure that the results were not an artifact of the peak alpha frequency estimation algorithm, pain sensitivity scores to the average was correlated, pain-free estimate of spectral power at each 0.2 Hz element within the 8-12 Hz range. For this analysis, spectra were z-scored in order to normalize total spectral power across individuals.

Next, it was determined whether pain-free, sensorimotor peak alpha frequency can accurately identify the most or least pain sensitive individuals. In the first analysis, a series of linear support vector machines (SVM) was used to perform leave-one-out, within-study classification (internal validation). To do so, pain scores from phasic heat pain, Capsaicin Heat Pain, and Capsaicin Heat Pain rekindle were averaged and, in separate tests, the top or bottom 10% of averaged pain scores were labelled as targets. A series of support vector machines were then trained to identify targets based on Visit 1 baseline, pain-free peak alpha frequency estimates from all but one individual (training set). Trained support vector machines were then used to predict whether the withheld participant was a target. Visit 1 data was used in order to maximize the size of the available dataset. Each participant served as the test exactly once and predictions were evaluated using F1 scores (harmonic mean of precision and recall; Sokolova & Lapalme, 2009; Lipton et al., 2014). F1 scores are often used when the proportions of two classes are uneven. To determine the full scope of prediction, this analysis was repeated by increasing the percentage of data labelled as a target in increments of 10% up to a maximum of 50% (i.e. median split of data). To evaluate F1 scores, a distribution of null F1 scores was generated by assigning targets at random and then performing the analysis described above. This procedure was carried out 10,000 times and obtained F1 scores were evaluated as significant if they were equal to or surpassed the 95th percentile of the null distribution.

In the second analysis, a single linear support vector machine was used to perform cross-study classification using data from the current study as the training set and data from an earlier study on Capsaicin Heat Pain sensitivity as the test set (external validation; Furman et al., 2018). Prior to analysis, peak alpha frequency estimates within each study were normalized to z-scores. Otherwise, details of this analysis were identical to those of the within-study classification analysis.

To examine whether pain-free, sensorimotor peak alpha frequency is reliable across Visits 1 and 2, estimates from each visit were compared using a paired t-test. Bayes factor analysis was used to determine whether the null hypothesis could be accepted (i.e. no change in peak alpha frequency between visits). Bayes factor analysis provides a method for assessing the relative evidence in favor of either the null or alternative hypothesis with a Bayes factor less than 0.33 or greater than 3 are taken as strong evidence in favor of the null and alternative hypotheses, respectively (Rouder et al., 2009); Bayes factor scores in-between these values are considered to provide no evidence in favor of either hypothesis. As an additional test of stability, peak alpha frequency estimates at Visits 1 and 2 were correlated with one another.

The stability of prolonged pain scores was assessed using a linear mixed effects model with subjects as random effects (intercept included) and Visit (Visit 1 vs Visit 2), Type (phasic heat pain vs. Capsaicin Heat Pain vs. Capsaicin Heat Pain Rekindle), and the Visit X Type interaction as fixed effects. It was of interest to determine whether scores change over time (main effect of Visit) and whether these changes were specific to individual tests (Visit X Type interaction). For each prolonged pain test, Bayes factor analysis was used to determine whether the null hypothesis could be accepted (i.e. no change in pain score between visits). Additionally, the stability of pain scores from each test was analyzed by correlating Visit 1 and Visit 2 pain scores.

To further test of the stability of pain-free, sensorimotor peak alpha frequency and prolonged pain scores, the correlation between pain-free, sensorimotor peak alpha frequency at Visit 1 and Visit 2 pain sensitivity was examined. To ensure that results were not an artifact of peak alpha frequency estimation algorithm, pain sensitivity scores to the average, pain-free estimate of spectral power at each 0.2 Hz element within the 8-12 Hz range was also correlated. Finally, it was tested whether pain-free, sensorimotor peak alpha frequency at Visit 1 could accurately identify the least and most pain sensitive individuals at Visit 2. As before, a series of leave-one-out SVMs were trained to identify the least or most pain sensitive individuals and then tested on the withheld participant. Performance was quantified by comparing the observed F1 score to a bootstrapped, null distribution of F1 scores.

Study C: All analyses were performed using custom scripts implemented in the Matlab environment (version R2013A). Statistical tests were conducted in Matlab or SPSS (Version 25).

First the periods of time when pain was present following nerve growth factor injection was determined. For each Study and on each day, pain scores were compared against 0 using one-sample t-tests. Given that detection of pain on each diary day was an a priori analysis of interest, it was elected not to apply corrections for multiple comparisons in this instance.

To determine whether pain-free, sensorimotor peak alpha frequency is associated with pain sensitivity it was first determined the maximum and average pain experienced across the days in which pain was statistically present for each Study (Days 1-17 for Study 1; Days 2-4 for Study 2). Day 0, pain-free Sensorimotor peak alpha frequency was then related to the maximum and average pain using separate Spearman correlations. To examine the unique relationship of Sensorimotor peak alpha frequency to each pain metric, a pair of partial correlations was performed between peak alpha frequency and one pain metric while controlling for the influence of the other pain metric.

To investigate how peak alpha frequency speed is associated with nerve growth factor pain over time, data was median-split according to Day 0 Sensorimotor peak alpha frequency to yield "slow" and "fast" peak alpha frequency groups. Pain scores were then analyzed using a linear mixed model with subjects as random effects (intercept modelled) and Group (Fast vs. Slow), Day (repeated measures; Days 1-17) and the Group×Day interaction as fixed effects.

Next, whether sensorimotor peak alpha frequency changes in response to the presence of nerve growth factor-induced pain was investigated. Sensorimotor peak alpha frequency estimates were submitted to a linear mixed effects model with subjects as random effects (intercept included) and Day (0, 2, 4, 6, and 14) as a fixed effect. The effect of Day using a planned, a priori linear contrast comparing Day 0 peak alpha frequency to all remaining, post-nerve growth factor peak alpha frequency estimates was investigated. In cases where significant effect was not found, the likelihood of the null hypothesis using Bayes factor analysis (Rouder et al., 2009) was tested. Bayes factor analysis provides a method for assessing the relative evidence in favor of either the null or alternative hypothesis. A Bayes factor less than 0.33 or greater than 3 are taken as strong evidence in favor of the null and alternative hypotheses, respectively; Bayes factor scores in between these values are considered to provide no evidence in favor of either hypothesis.

To further test the stability of sensorimotor peak alpha frequency, Spearman correlations were performed between all possible pairs of peak alpha frequency estimates. Corrections for multiple tests (10 possible pairs) were made according to the Bonferonni method, yielding a significance threshold of $\rho=0.005$. Additionally, the reliability of sensorimotor peak alpha frequency using Chronbach's $\alpha$ was investigated.

To test whether changes in sensorimotor peak alpha frequency after nerve growth factor injection ($\Delta$peak alpha frequency) are related to average pain sensitivity, $\Delta$PAF by subtracting pain-free, sensorimotor peak alpha frequency from the average, post-nerve growth factor sensorimotor peak alpha frequency recorded on Days 2, 4, 6 and 14 was first calculated. Then a Spearman correlation between $\Delta$PAF and average pain was performed.

Example 2

Pain Intensity and the Capsaicin Heat Pain Model

Prolonged pain was evoked using capsaicin heat pain model on the forearm. Six participants in the Pain group were excluded for failing to develop moderate pain to the capsaicin (consistent with previous observations that about 25% of people are insensitive to capsaicin (Liu et al., 1998; Walls et al. 2017) and three participants in the Non-Pain group were excluded for developing pain that was rated as greater than 10 on average. For the remaining 21 participants in the Pain group, mean pain intensity was 56.01 (S.D.±16.96). For the Non-Pain group, which underwent identical procedures without capsaicin exposure, mean pain was 1.99 (S.D.±2.68).

An independent samples t-test comparing these two groups confirmed that the presence of capsaicin led to heightened pain in response to a warm stimulus, $t(36)=11.86$, $\rho<0.01$. This test was also performed for the entire sample (including subjects not responding to the C-HP model and subjects who reported pain with just the warm stimulus), $t(42)=6.78$, $\rho<0.01$. This difference appears to be a result of the capsaicin rather the heat stimulus given that applied temperatures were not significantly different between the group (Pain Group: mean=38.52, std=2.71, range=32-41; Non-Pain group: mean=38.25, std=1.57, range=37-41; $t(33)=0.36$, $\rho=0.72$). Furthermore, there was no difference between the groups in terms of HPT (Pain Group: mean=43.67, std=2.22, range=39-47; Non-Pain group: mean=43.52, std=2.74, range=39-50; t(36)=0.86, ρ=0.17) or difference between HPT and thermode temperature (Pain Group: mean=5.21, std=2.16, range=1-9; Non-Pain Group: mean=5.44, std=2.13, range=2-9; t(33)=0.75, ρ=0.31). In addition, there was no relationship between thermode temperature and pain intensity in the Pain group (r=−0.25, ρ=0.30) or Non-Pain group (r=−0.02, ρ=0.94).

Example 3

Figure 2A:
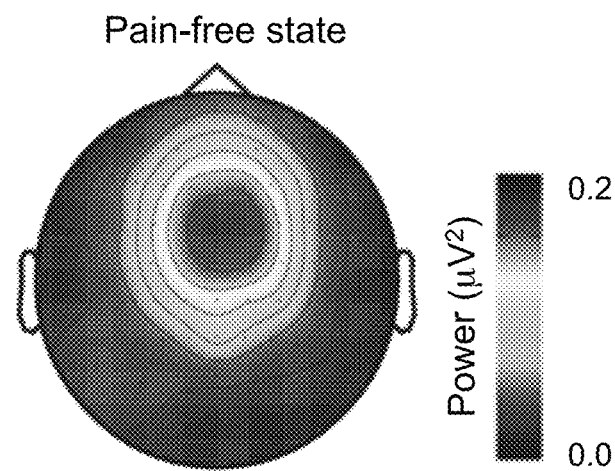
FIGS. 2A-2F illustrate the relationship between peak alpha frequency and prolonged pain.
Figure 2B:
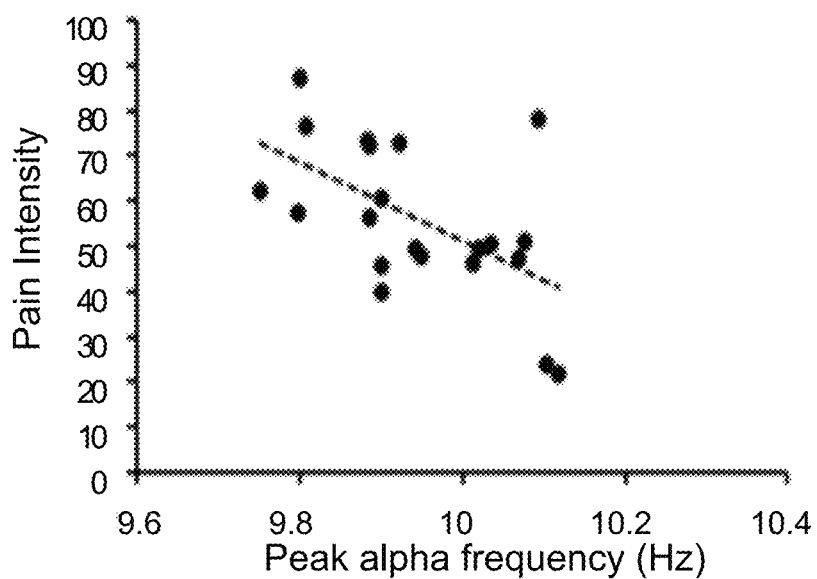
Figure 2C:
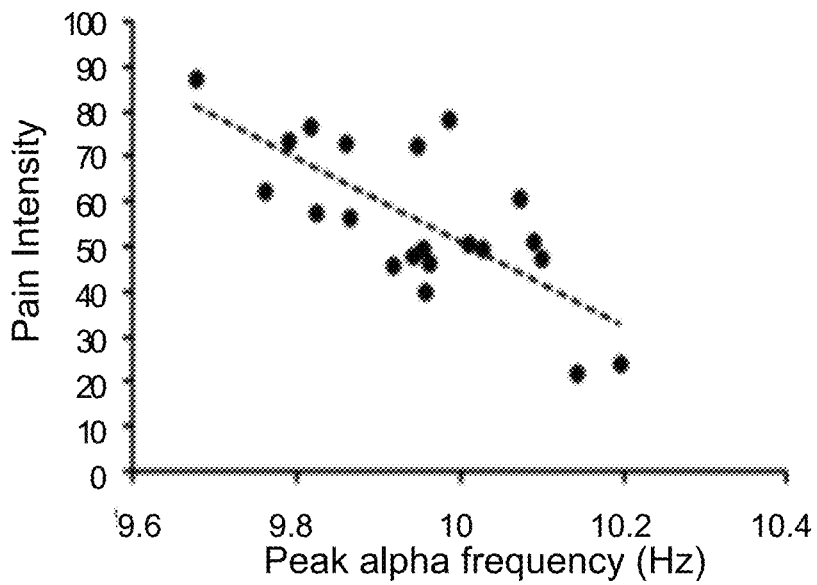

Peak Alpha Frequency at Pain-Free and Prolonged Pain States Correlated with Pain Intensity The topography of the central alpha component used in the analysis, averaged across Pain group participants can be seen in FIG. 2A. Firstly, presence of a correlation between central component peak alpha frequency recorded during the pain-free state and pain intensity was determined. It was observed that pain-free state central component peak alpha frequency correlated negatively with pain intensity (r=−0.57, ρ=0.01); that is, the lower an individual's average central peak alpha frequency, the greater their pain (FIG. 2B). This provides initial evidence that an individual's central peak alpha frequency in the absence of a noxious stimulus may play a role in determining an individual's vulnerability to a prolonged pain. There was not a significant relationship between the pain-free state power estimate of the central component PAF (peak alpha frequency power) and subsequent pain intensity ratings (r=0.23, ρ=0.32). This was followed by assessment of whether central component peak alpha frequency during the prolonged pain state was related to pain intensity. It was determined that central peak alpha frequency during prolonged pain correlated negatively with pain intensity (r=−0.73, ρ<0.01); that is, slower peak alpha frequency was associated with greater pain intensity (FIG. 2C). The relationship between prolonged pain state central component peak alpha frequency and pain intensity remained significant when controlling for thermode temperature using a partial correlation (r=−0.72, ρ<0.01), suggesting that this relationship is driven by factors other than the magnitude of the sensory stimulus alone. No significant relationship was observed between central component peak alpha frequency power during prolonged pain and pain intensity (r=0.10, ρ=0.67), highlighting the importance of peak alpha frequency rather than peak alpha frequency power in prolonged pain.

Example 4

Figure 2D:
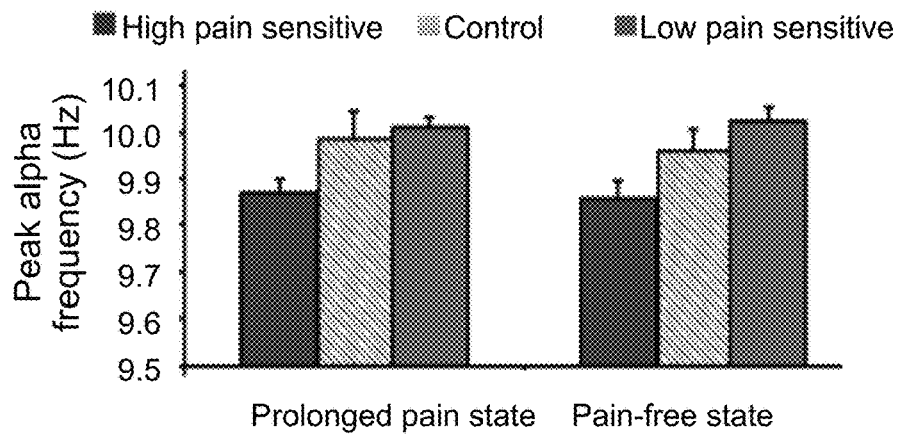
Figure 2E:
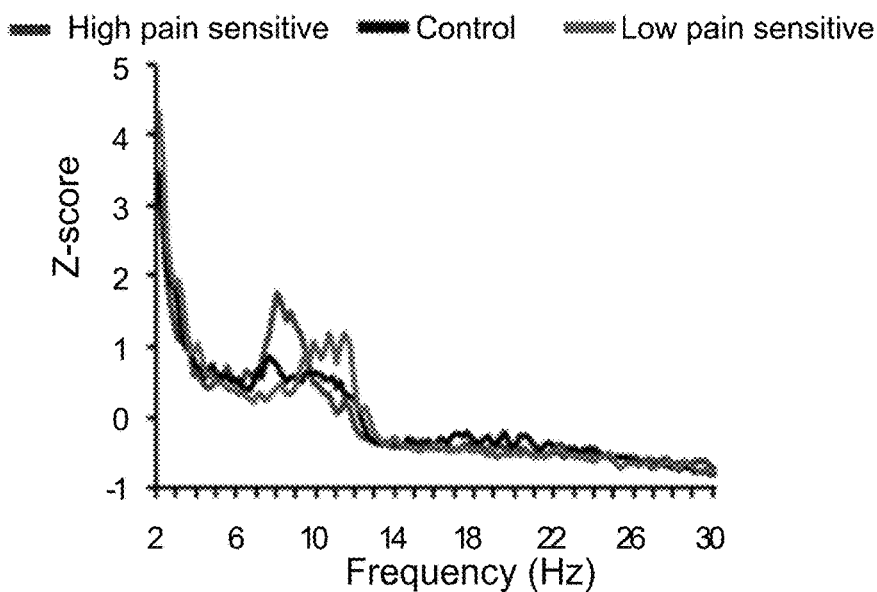
Figure 2F:
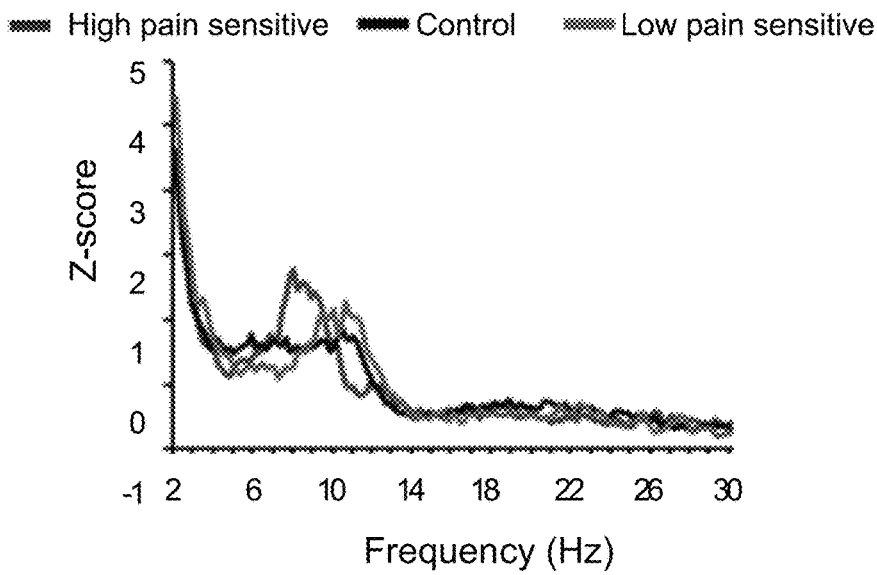

Peak Alpha Frequency can Distinguish Between High and Low Pain Sensitive Individuals The foregoing correlations suggest that the frequency of central alpha activity at baseline and during pain is related to the pain intensity. To investigate this relationship further a median split of Pain group participants into high and low pain sensitivity groups was performed, based on their reported pain intensity. The difference in central peak alpha frequency between Non-Pain (control), high pain sensitive, and low pain sensitive groups was statistically assessed using a 2×2 Repeated Measures ANOVA with group (controls vs high pain sensitive vs low pain sensitive)×state (pain-free vs prolonged pain state) serving as between- and within-subject factors. The main effect of group was significant, F(2,32)=3.48, ρ=0.04. As can be seen qualitatively in FIG. 2D, the low pain sensitive group displayed the fastest central peak alpha frequency across both states, the high pain sensitive group displayed the slowest central peak alpha frequency across both states, and the control group displayed peak alpha frequency somewhere in between the two; this last observation likely reflects that the Non-pain group contains some combination of high and low pain sensitive individuals. Critically, neither the main effect of state F(2, 32)=0.127, ρ=0.72, nor the group×state interaction F(2,32)= 0.397, ρ=0.68 were significant. Bonferroni corrected pairwise comparisons revealed a significant difference in peak alpha frequency between high and low pain sensitive groups in the pain-free state, ρ=0.026. Visual inspection of the central component power spectra revealed differences between groups were largely restricted to the alpha frequency domain, further highlighting the specific importance of alpha in the model of prolonged pain (FIGS. 2E-2F).

Example 5

Peak Alpha Frequency Shift from Pain-Free to Prolonged Pain States (ΔPAF) was Associated with Pain Intensity Central component peak alpha frequency in the pain-free and prolonged pain states were strongly correlated (r=0.86, ρ<0.05, FIG. 3A). While this suggests peak alpha frequency is largely stationary, it does not rule out the possibility that small changes in peak alpha frequency also play a role in the experience of pain. To investigate this the peak alpha frequency shift (ΔPAF) was calculated as the difference between central component peak alpha frequency during prolonged pain and pain-free states). ΔPAF negatively correlated with pain intensity (r=−0.50, ρ=0.02, FIG. 3B), indicating that peak alpha frequency slowing is associated with increased pain. The average, absolute peak alpha frequency shift across individuals was 0.05 Hz (s.d.=0.05).

Example 6

Peak Alpha Frequency and ΔPAF Provide Distinct Information about Pain Intensity

Despite showing quantitatively similar relationships to pain intensity, central component ΔPAF and pain-free state central component peak alpha frequency were uncorrelated (r=0.05, ρ=0.82, FIG. 3C), suggesting that pain-free state peak alpha frequency and ΔPAF represent distinct elements of pain sensitivity. To formally test the degree to which pain-free state central peak alpha frequency and central ΔPAF independently predict pain sensitivity, a hierarchical regression was performed using pain sensitivity as the dependent variable and pain-free state, central component peak alpha frequency and central component ΔPAF as independent variables entered first and second, respectively, into the model. The full regression model significantly predicted pain intensity (F(2,18)=10.72, ρ<0.01) with an adjusted $R^2$ of 0.493, indicating that pain-free state central peak alpha frequency and ΔPAF accounted for nearly 50% of the variance in pain intensity. Importantly, addition of pain-free state peak alpha frequency (β=−0.543, ρ<0.01) and ΔPAF (β=−0.47, ρ<0.01) each yielded significant changes to the $R^2$ of the regression model (Pain-free state ΔR2=0.323, ΔF=9.065, ρ<0.01; Shift $\Delta R^2$=0.221, ΔF=8.70, ρ<0.01). Taken together, this analysis provides evidence that peak alpha frequency characteristic to an individual, indexed by pain-free state central component peak alpha frequency, and the extent to which peak alpha frequency is modulated by prolonged pain, indexed by central component ΔPAF, are distinct mechanisms whose action play an important role in determining pain sensitivity.

Example 7

Peak Alpha Frequency and ΔPAF can be Used to Predict Pain Intensity

Figure 4A:
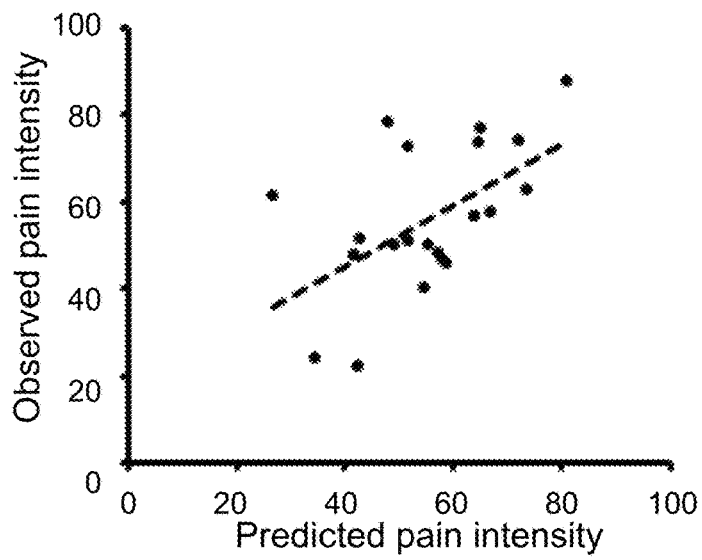
FIGS. 4A-4C show that individual pain sensitivity can be predicted.
Figure 4B:
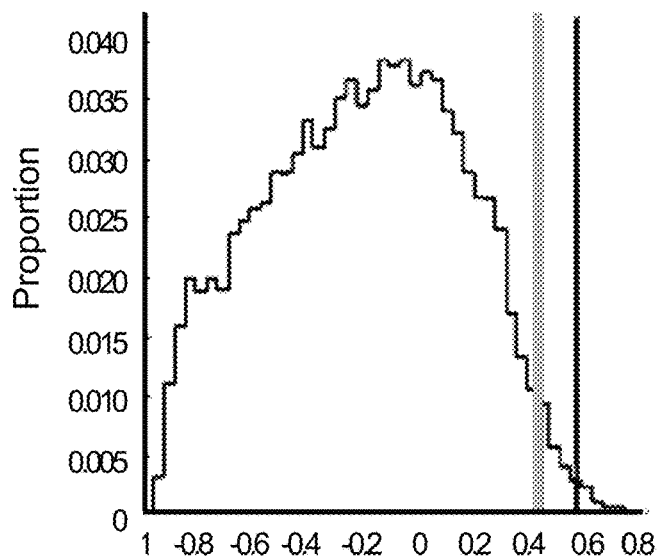
Figure 4C:
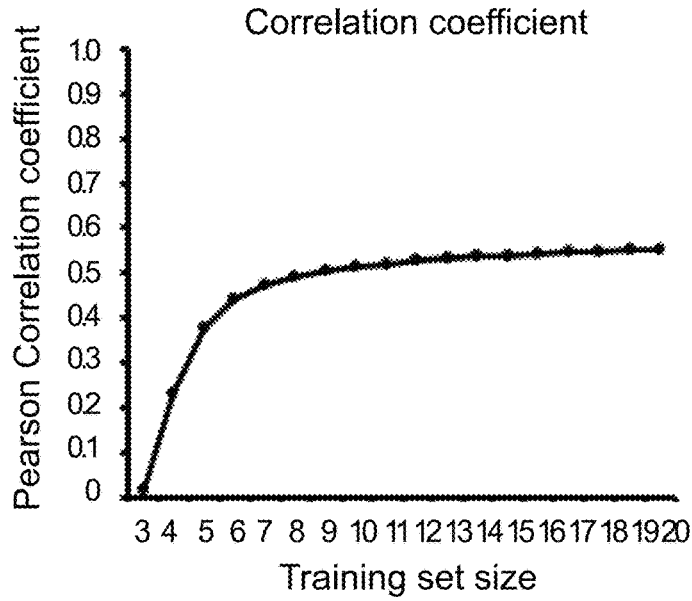

To further assess the robustness of the finding that pain-free state central component peak alpha frequency and its changes in response to the C-HP model are predictive of pain sensitivity, a leave-one-out regression analysis was performed. Briefly, a series of regression models were generated using pain-free state peak alpha frequency and ΔPAF from 20 of the 21 individuals (training set) and then used the resulting model to generate a pain prediction for the withheld test individual. Each individual served as the test for exactly one regression model, yielding a total of 21 regression models and 21 predictions. The Pearson correlation between predicted pain intensity and actual pain intensity was $r=0.55$ (FIG. 4A). This observed relationship surpassed the 95th percentile of a null distribution of r values generated using permuted peak alpha frequency measures and pain intensity ($r=0.22$), indicating that the two peak alpha frequency measures can be used to predict pain intensities at a level greater than chance (FIG. 4B). To ensure that the apparent ability of pain-free state central component peak alpha frequency and central component ΔPAF to predict pain intensity was not specific to this leave one out approach, the above analysis were repeated with training set sizes that ranged from 3 individuals to 20. Within a training set size, separate regression models were generated for all the unique combinations of participants; models were then evaluated together as the Pearson correlation between all predicted pain intensity and all observed pain intensity. As can be seen in FIG. 4C, prediction became stable around a training set size of 6 ($r=0.49$) and increased a relatively small amount to the maximum training size of 20 (0.55). This suggests that the ability to predict future pain intensity from pain-free state peak alpha frequency and ΔPAF to predict pain intensity is robust and not altered by the cross-validation procedures employed.

Example 8

Sensorimotor Peak Alpha Frequency is Reliably Predicts Thermal, Prolonged Pain Sensitivity From the initial cohort of 61 individuals, two individuals were removed due to abnormal pain ratings: one participant fell asleep during ratings while another participant provided extremely high pain ratings in the absence of any noxious stimuli indicating that they may been confused by the rating scheme. One additional participant who experienced a change in Capsaicin Heat Pain score, +69.26, that was 3.82 standard deviations greater than the average Capsaicin Heat Pain change (average change=1.76, S.D.=17.64) was excluded. No other change in Capsaicin Heat Pain scores was greater than 2.05 standard deviations above the mean (range=+37.96 to −31.05).

From the remaining 58 participants (Table 1), 33 participants were classified as Capsaicin Heat Pain responders (Capsaicin Heat Pain score>10), 10 participants were classified as high tolerance individuals (Capsaicin Heat Pain and phasic heat pain scores<10), and 15 participants were classified as Capsaicin Heat Pain non-responders (phasic heat pain score>10 & Capsaicin Heat Pain score<10). Due to a technical error, EEG data was lost for one Capsaicin Heat Pain responder at Visit 1; Visit 1 data for this individual was only included in prolonged pain analyses. Of the 58 individuals providing data at Visit 1, a total of 43 individuals also provided data at Visit 2, of which 32 had been classified as a Capsaicin Heat Pain responder or high tolerance individual. Capsaicin Heat Pain rekindle data for one participant at Visit 2 was not collected. Unless otherwise stated, analyses only include data from high tolerance and CHP responder individuals.

TABLE 1

Summary of exclusions and participants contributing data at each testing visit

| | Visit 1 | | | Visit 2 | | |
|---|---|---|---|---|---|---|
| Participant Type | Capsaicin Responder | Capsaicin Non-Responder | High Pain Tolerance | Capsaicin Responder | Capsaicin Non-Responder | High Pain Tolerance |
| Total Participants | 35 19 Female | 15 6 Female | 11 5 Female | 27 14 Female | 11 4 Female | 8 3 Female |
| Exclusions | | | | | | |
| EEG Technical Error | 1 1 Female | 0 | 0 | 0 | 0 | 0 |
| Abnormal Pain Ratings | 1 1 Female | 0 | 1 0 Female | 1 1 Female | 0 | 1 0 Female |
| Abnormal CHP Change | 1 1 Female | 0 | 0 | 1 1 Female | 0 | 0 |
| Participants Remaining | 32 16 Female | 15 6 Female | 10 5 Female | 25 12 Female | 11 4 Female | 7 3 Female |

Figure 5A:
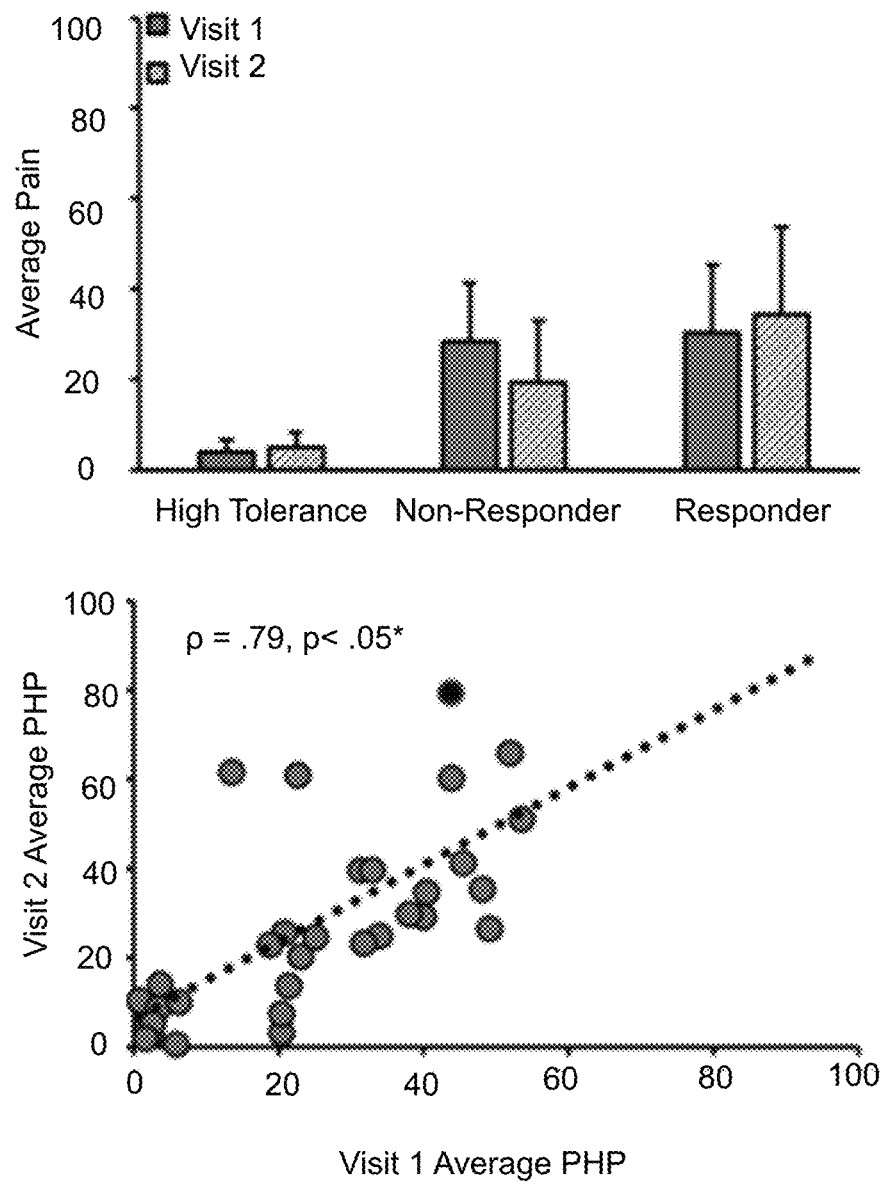
FIGS. 5A-5C shows that pain ratings broken down by prolonged pain test, pain response classification, and visit. Bar graphs reflect means and error bars reflect+1 standard deviation. Scatter plots only include data from Capsaicin Heat Pain responders and high tolerance individuals. Asterisks (*) reflect, where applicable, significance after statistical correction for multiple tests ($\rho=0.0167$).
Figure 5B:
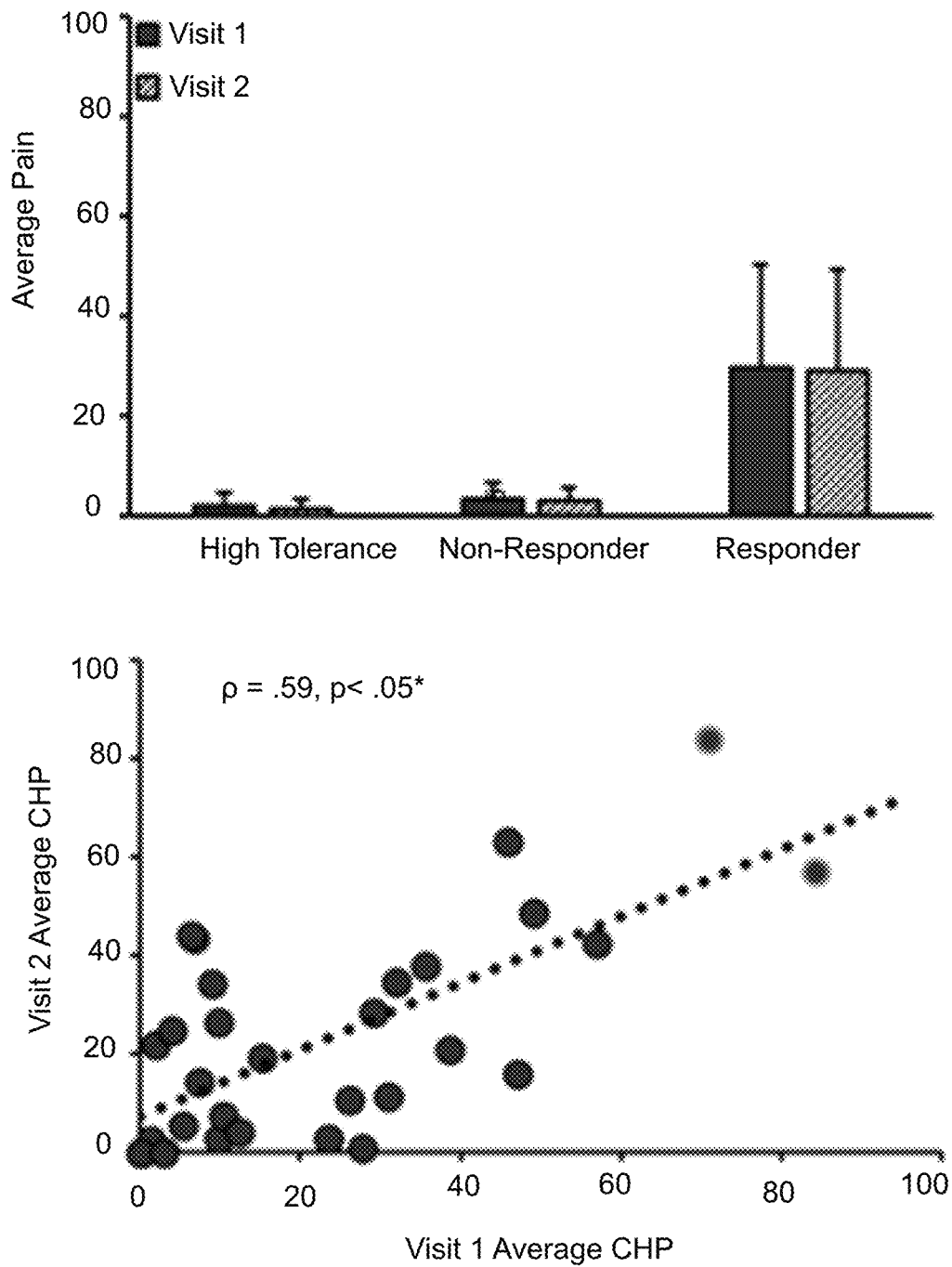
Figure 5C:
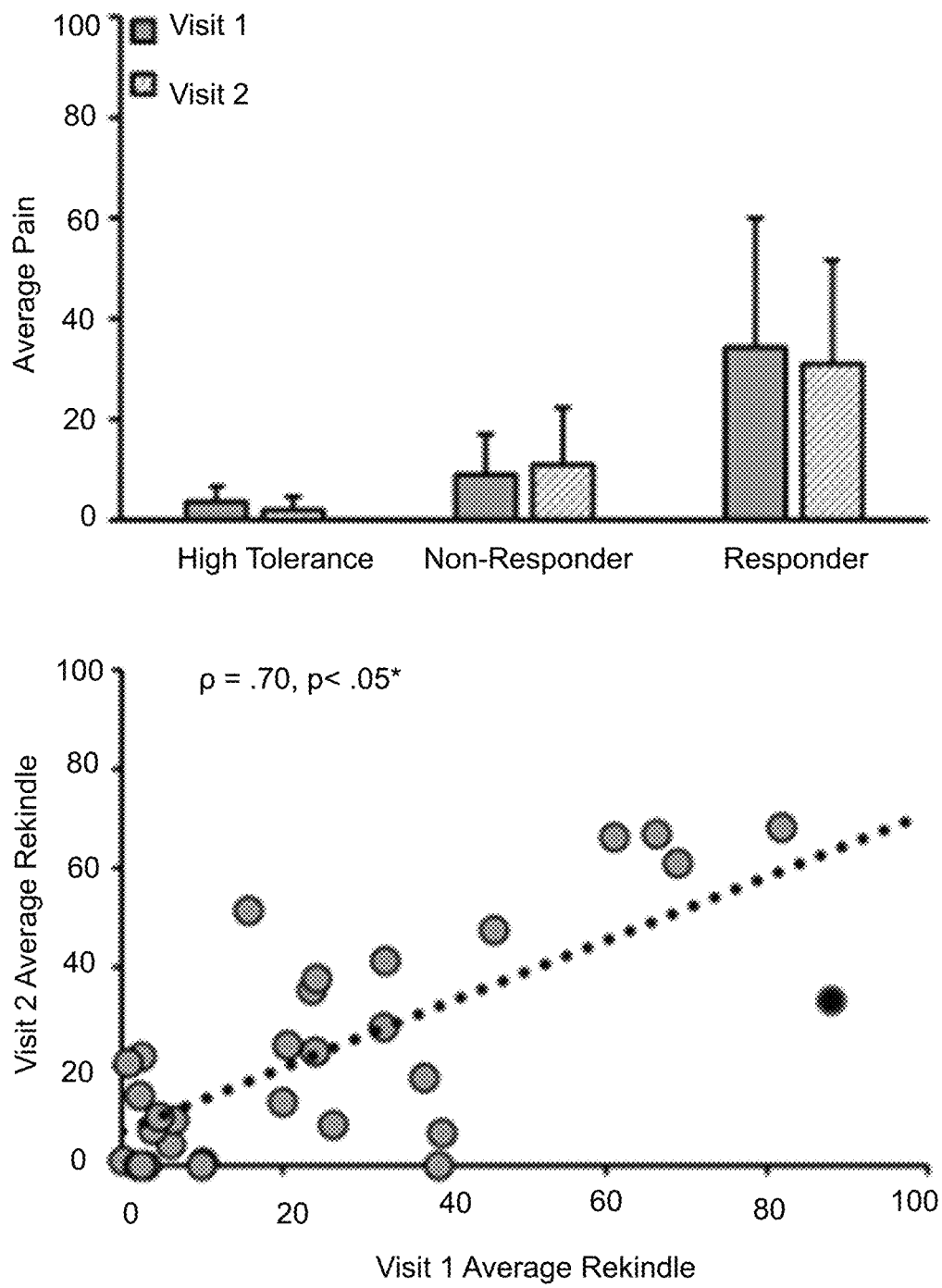

A summary of prolonged pain scores for each pain response classification is presented in FIG. 5. Both phasic heat pain and Capsaicin Heat Pain produced sensitization, a hallmark of prolonged pain, and similar amounts of pain in males and females. Correlations between all possible pairs of tests were significant (Table 2) and this conclusion held when analyses were repeated while including all participants regardless of pain response classification. Reliability analysis further revealed that sensitivity was consistent across prolonged pain tests, Chronbach's α=0.91 (Visit 1 alone, α=0.82, Visit 2 alone, α=0.83). Including all subjects, regardless of pain response classification, did not alter this finding, Chronbach's α=0.90 (Visit 1 alone, α=0.77, Visit 2 alone, α=0.83). Thus, Capsaicin Heat Pain and phasic heat pain appear to sample similar prolonged pain processes.

TABLE 2

Spearman correlation coefficients (p values) between prolonged pain tests at each testing visit.

|  | Visit 1 | | Visit 2 | |
| --- | --- | --- | --- | --- |
|  | CHP | CHP Rekindle | CHP Rekindle | CHP |
| PHP | .52 (<.05*) | .50 (<.05*) | .58 (<.05*) | .77 (<.05*) |
| CHP |  | .88 (<.05*) | .78 (<.05*) |  |

Asterisks (*) reflect, where applicable, significance after statistical correction for multiple tests (p = .0167)

Figure 6A:
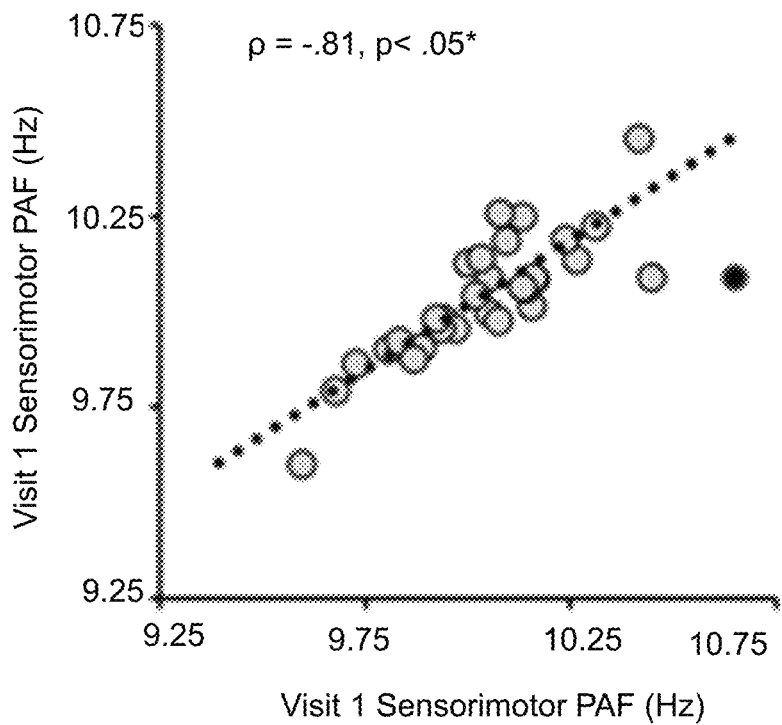
FIGS. 6A-6B shows that pain-free, sensorimotor peak alpha frequency estimates are strongly correlated across Visits. Note that Visit 2 occurred, on average, 7.8 weeks after Visit 1. Pain-free, sensorimotor peak alpha frequency and prolonged pain models are stable across Visits
Figure 6B:
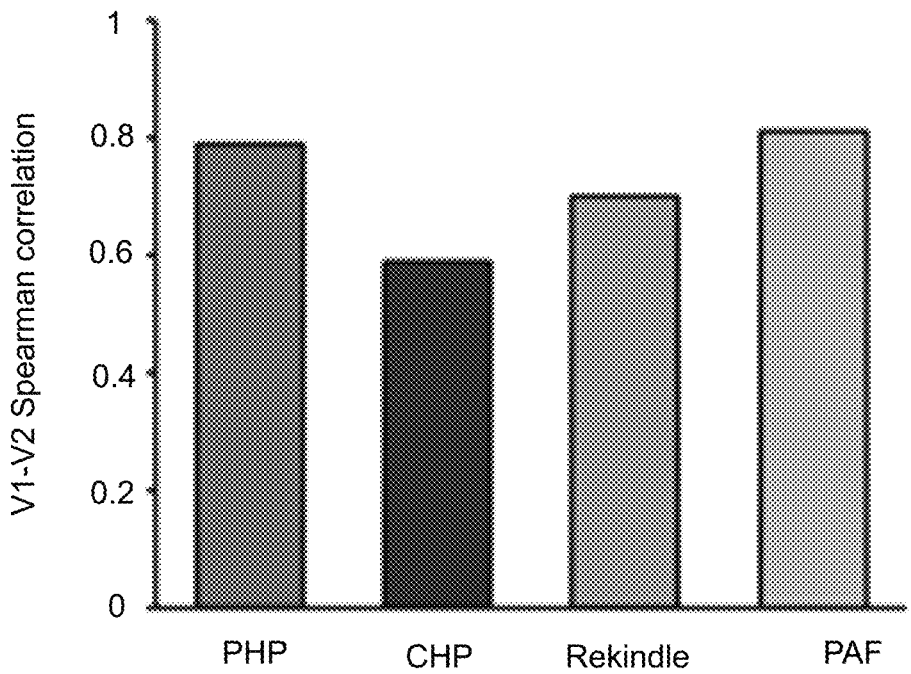
Figure 7A:
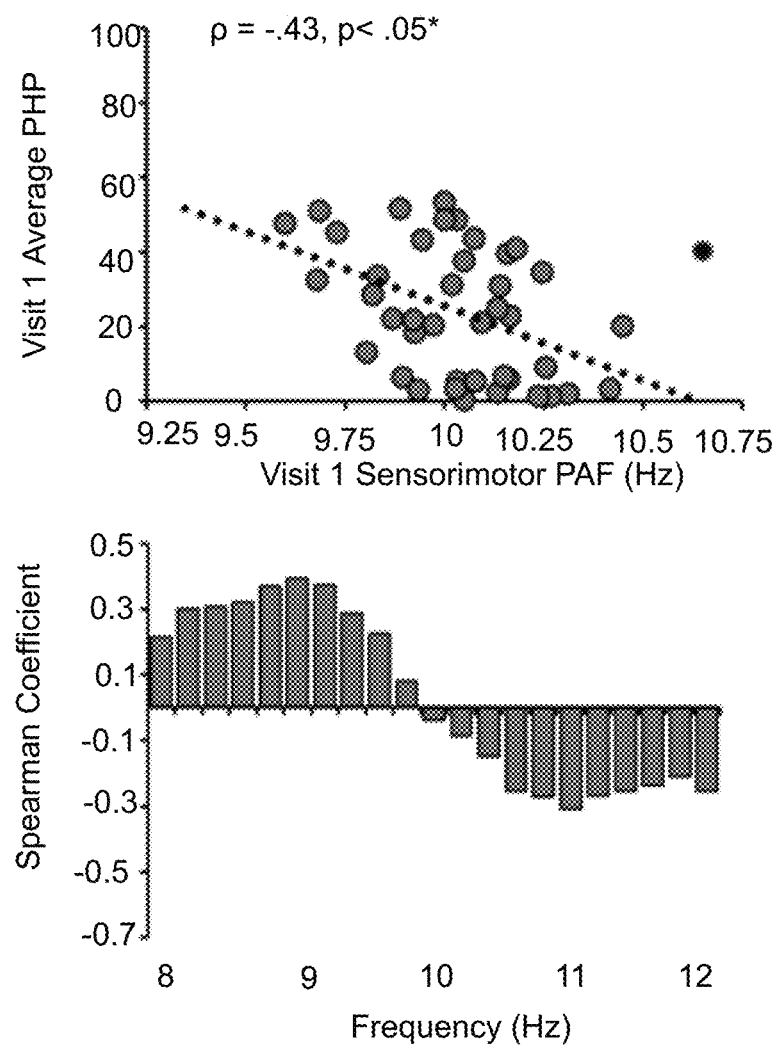
FIGS. 7A-7C shows that visit 1 pain-free, sensorimotor peak alpha frequency is correlated with sensitivity to all three Visit 1 prolonged pain tests. Bar graphs below each scatter plot reflect Spearman correlation coefficients between Visit 1 pain scores and Visit 1 estimates of pain-free power at each 0.2 Hz bin within the 8-12 Hz range. For all three tests, frequency elements below 10 Hz are positively associated with pain sensitivity while frequency elements above 10 Hz are negatively associated with pain sensitivity. Asterisks (*) reflect, where applicable, significance after statistical correction for multiple tests ($\rho=0.0167$).
Figure 7B:
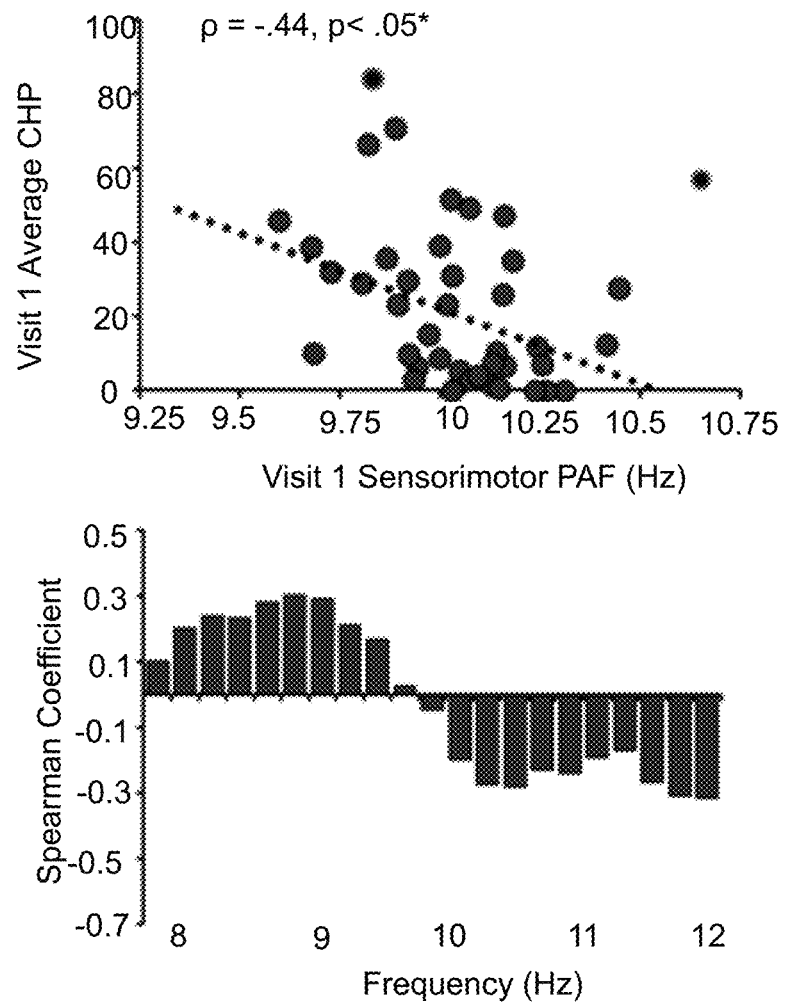
Figure 7C:
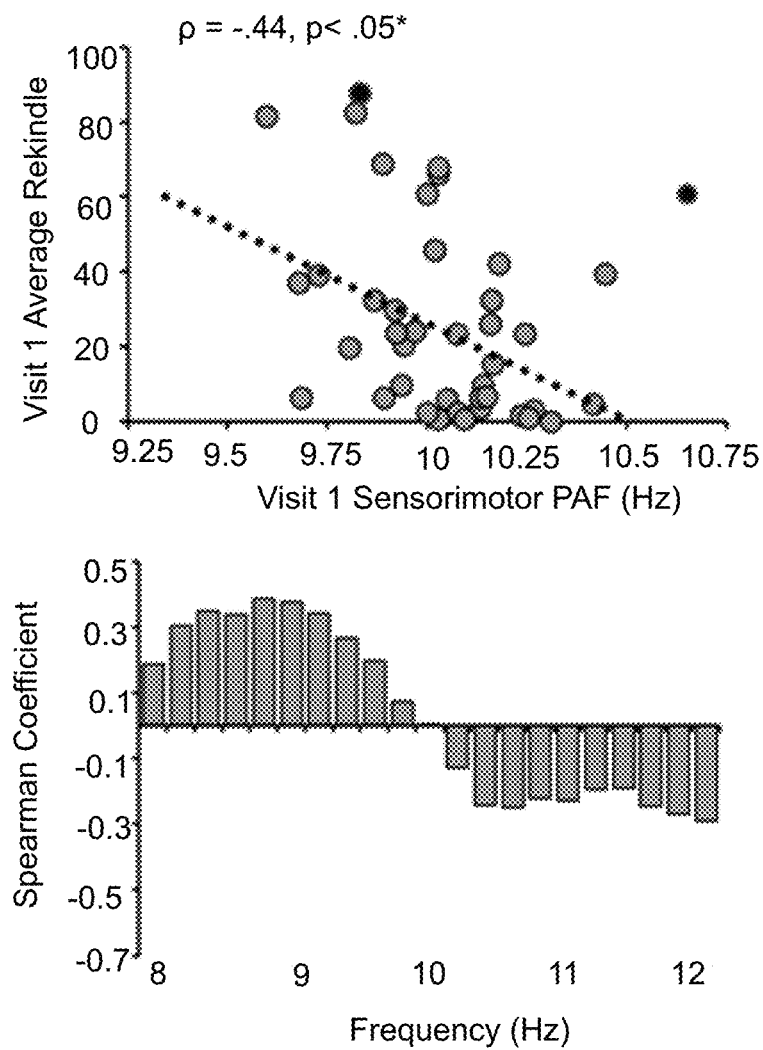

Visit 1, pain-free, sensorimotor ROI spectra from all participants are presented in FIGS. 6A-6B. At Visit 1, pain-free, sensorimotor peak alpha frequency predicted pain sensitivity to all three prolonged pain tests, phasic heat pain: Spearman $\rho=-0.43$, $p<0.05$ corrected; Capsaicin Heat Pain: Spearman $\rho=-0.44$, $p<0.05$ corrected; Capsaicin Heat Pain rekindle sensitivity, Spearman $\rho=-0.44$, $p<0.05$ corrected (FIG. 6B). Similar results were obtained for phasic heat pain when a partial correlation was used to account for variability in the thermode temperature used during phasic heat pain, Spearman $\rho=-0.40$, $p<0.05$ corrected, or when all participants regardless of pain response classification was included, Spearman $\rho=-0.34$, $p<0.05$ corrected. Expanding the peak alpha frequency calculation range to 8-12 Hz did not greatly impact the relationship for any prolonged pain test, phasic heat pain: Spearman $\rho=-0.38$, $p<0.05$ corrected; Capsaicin Heat Pain: Spearman $\rho=-0.34$, $p=0.03$, Capsaicin Heat Pain rekindle: $-0.38$, $p<0.05$ corrected. Furthermore, inspection of the relationship between pain sensitivity and power at each frequency element within the alpha range demonstrate that these results are not an artifact of the peak alpha frequency calculation method: for each test, slower (8-9.5 Hz) elements were positively associated with pain sensitivity while faster (10.5-12 Hz) elements were negatively associated with pain sensitivity (FIGS. 7A-7B, lower). No evidence of sex effects on the relationship of peak alpha frequency to either phasic heat pain, Capsaicin Heat Pain, or Capsaicin Heat Pain rekindle was found. Interestingly, the relationship between peak alpha frequency and prolonged pain sensitivity was apparent at nearly every scalp channel even when volume conduction was accounted for with a surface Laplacian transformation.

Figure 8A:
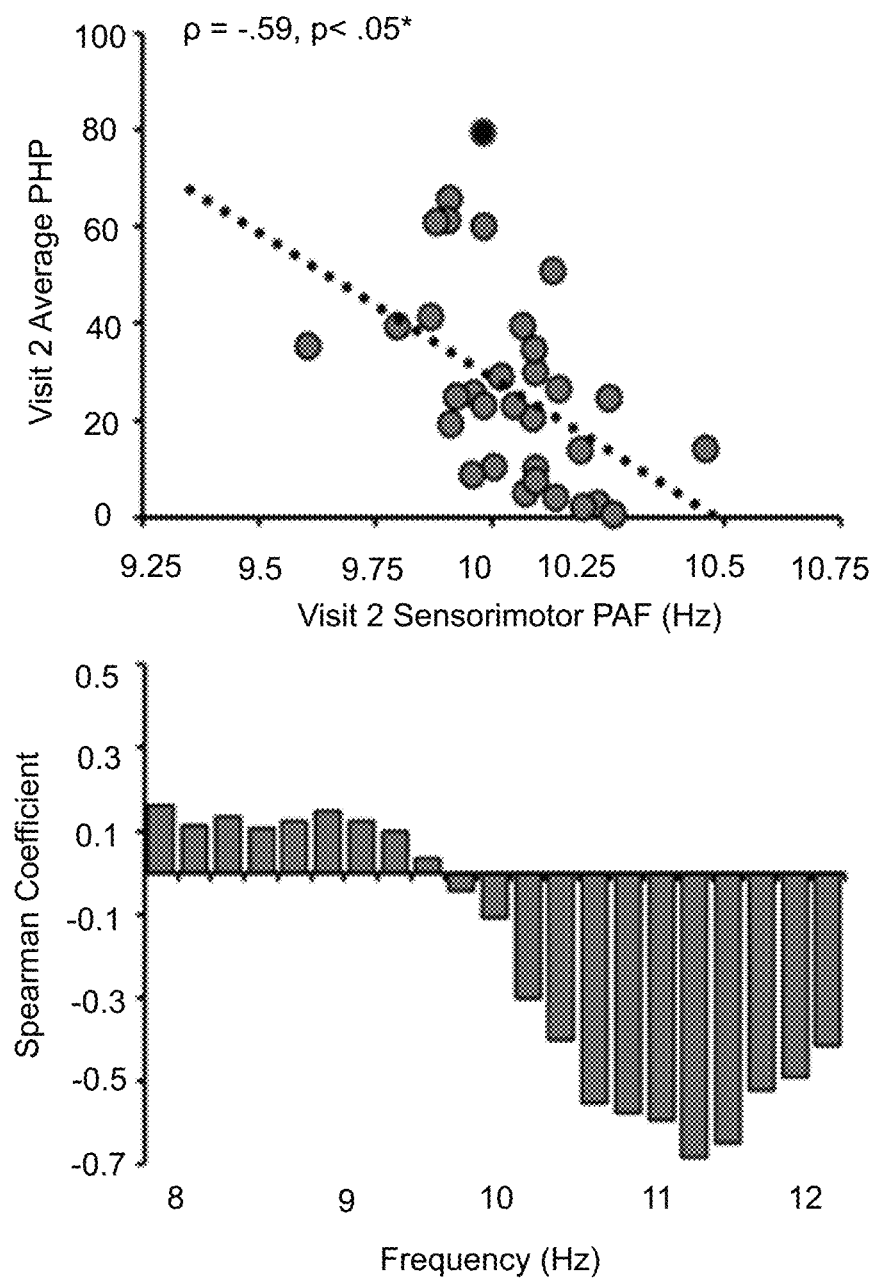
FIGS. 8A-8C shows that visit 2 pain-free, sensorimotor peak alpha frequency is significantly correlated with sensitivity to all three Visit 2 prolonged pain tests. Bar graphs below each scatter plot reflect Spearman correlation coefficients between Visit 2 pain scores and Visit 2 estimates of pain-free power at each 0.2 Hz bin within the 8-12 Hz range. For all three tests, frequency elements below 10 Hz are positively associated with pain sensitivity while frequency elements above 10 Hz are negatively associated with pain sensitivity. Asterisks (*) reflect, where applicable, significance after statistical correction for multiple tests ($\rho=0.0167$).
Figure 8B:
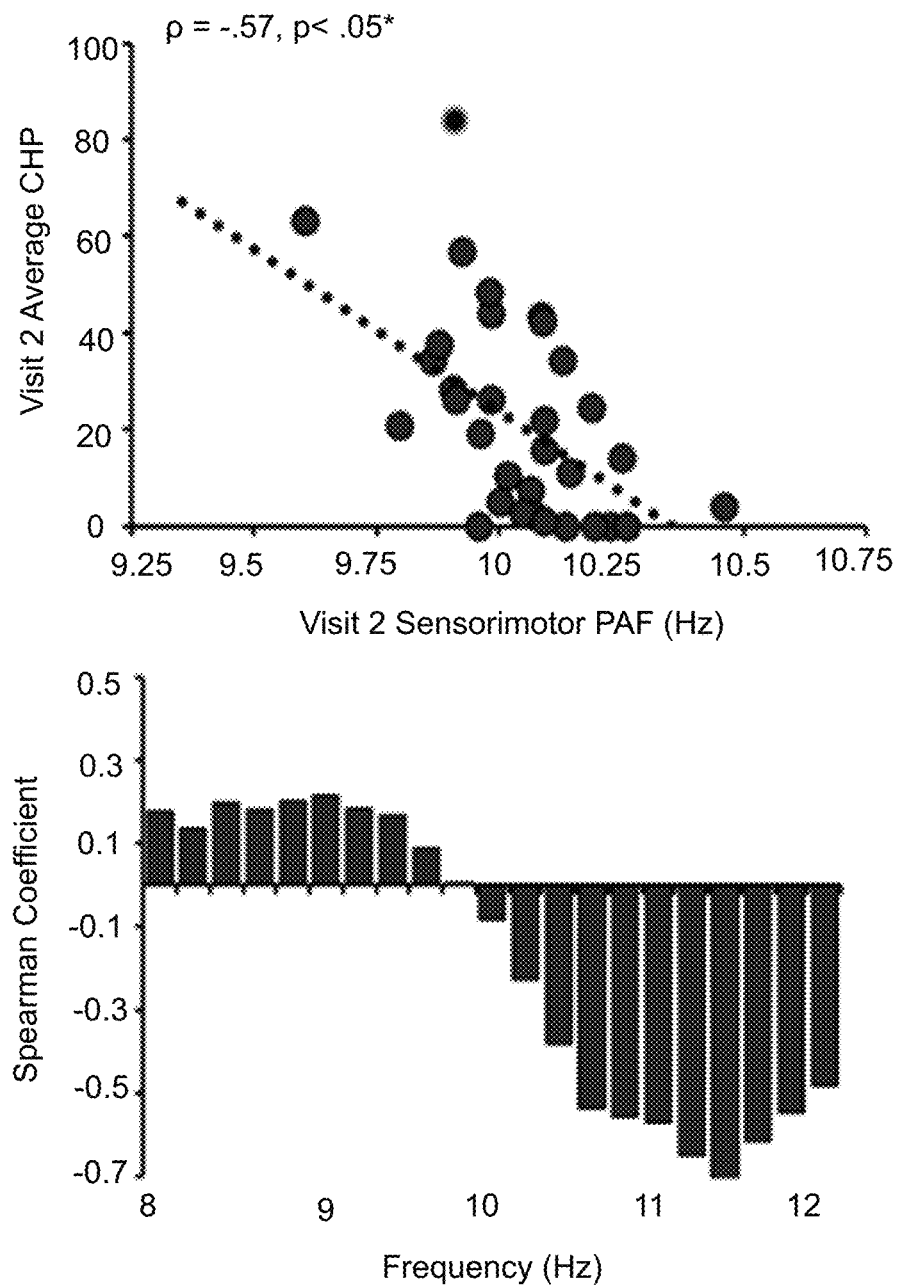
Figure 8C:
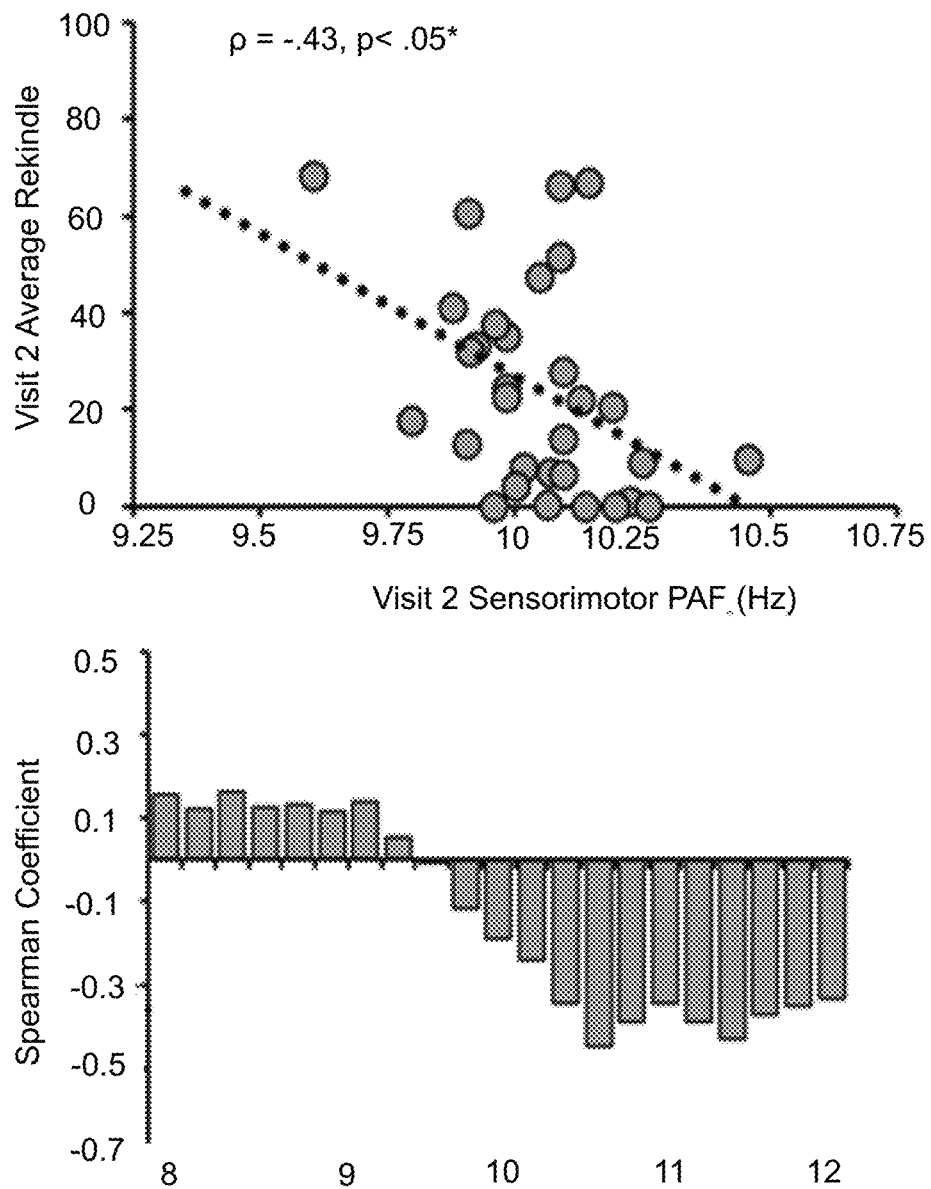

At Visit 2, pain-free, sensorimotor peak alpha frequency again predicted pain sensitivity to all three prolonged pain tests, phasic heat pain: Spearman $\rho=-0.59$, $p<0.05$ corrected; Capsaicin Heat Pain: Spearman $\rho=-0.57$, $p<0.05$ corrected; Capsaicin Heat Pain rekindle sensitivity, Spearman $\rho=-0.43$, $p<0.05$ corrected (FIGS. 8A-8C). As before, phasic heat pain outcomes remained stable when either accounting for thermode temperature with a partial correlation, Spearman $\rho=-0.55$, $p<0.05$ corrected, or including all 43 participants regardless of pain response classification, Spearman $\rho=-0.37$, $p<0.05$ corrected. Expanding the peak alpha frequency calculation range to 8-12 Hz did not impact peak alpha frequency's relationship to any test, phasic heat pain: Spearman $\rho=-0.51$, $p<0.05$ corrected; Capsaicin Heat Pain: Spearman $\rho=-0.58$, $p<0.05$ corrected, Capsaicin Heat Pain rekindle: Spearman $\rho=-0.44$, $p<0.05$ corrected, and correlations between pain and power across the alpha range once again revealed an association of slow and fast ranges with heightened and decreased pain sensitivity, respectively (FIGS. 8A-8C, lower). As in Visit 1, there did not appear to be an influence of sex on the relationship between peak alpha frequency and any of the prolonged pain tests and this relationship was evident across the entire scalp.

Example 9

Sensorimotor Peak Alpha Frequency and Prolonged Pain Sensitivity are Stable Over Time One possible explanation for the presence of a reliable relationship between pain-free, sensorimotor peak alpha frequency and prolonged pain sensitivity at Visits 1 and 2 is that both measures are themselves stable over time. In line with this premise, Visit 1 (mean=10.04, S.D.=0.20) and Visit 2 (mean=10.04, S.D.=0.16) estimates of pain-free, sensorimotor peak alpha frequency were not significantly different, t(29)=0.32, $p=0.75$, and Bayes factor analysis supported the null hypothesis of no differences between the two, Bayes Factor<0.01. These results did not change when all participants regardless of pain response classification t(40)=0.34, $p=0.73$, Bayes Factor <0.01 were included. What's more, Visit 1 and Visit 2 estimates of pain-free, sensorimotor peak alpha frequency were strongly correlated, Spearman $\rho=0.81$, $p<0.05$ (FIGS. 6A-6B); this finding did not change when all participants regardless of pain response, Spearman $\rho=0.82$, $p<0.05$, or expanded the peak alpha frequency calculation range to 8-12 Hz, Spearman $\rho=0.86$, $p<0.05$ were included.

Similarly, a linear mixed effects model revealed that prolonged pain sensitivity did not change over time with neither the main effect of Visit, $F_{(1,161.32)}=0.13$, $p=0.72$, nor the Visit×Pain Type interaction, $F_{(2,113.244)}=0.26$, $p=0.77$, reaching significance. Bayes factor analysis failed, however, to support either the null or alternative hypothesis for any prolonged pain test, phasic heat pain: Bayes Factor=1.19, Capsaicin Heat Pain: Bayes Factor=0.71, Capsaicin Heat Pain Rekindle: Bayes Factor=0.74. Visit 1 and Visit 2 pain scores were correlated for all three prolonged pain tests, phasic heat pain, $\rho=0.79$, $p<0.05$ corrected, Capsaicin Heat Pain, $\rho=0.59$, $p<0.05$ corrected, and Capsaicin Heat Pain rekindle, $\rho=0.70$, $p<0.05$ corrected (FIGS. 5A-5C), and remained so when the dataset to include Capsaicin Heat Pain non-responders, phasic heat pain: $\rho=0.74$, $p<0.05$ corrected; Capsaicin Heat Pain: $\rho=0.69$, $p<0.05$ corrected, Capsaicin Heat Pain Rekindle, $\rho=0.68$, $p<.05$ corrected was expanded.

Example 10

Figure 9A:
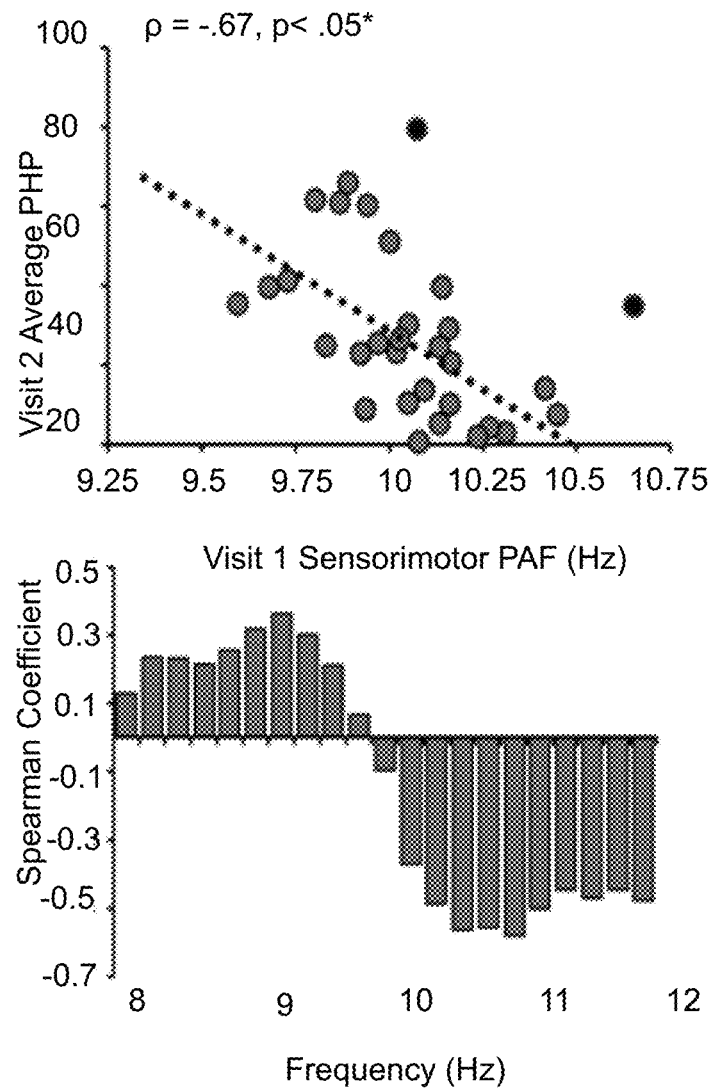
FIGS. 9A-9C shows that visit 1 pain-free, sensorimotor peak alpha frequency predicts sensitivity to all three Visit 2 prolonged pain tests. Note that Visit 2 occurred, on average, 7.8 weeks after Visit 1. Off-color data points represent statistical outliers not included in analyses and dotted lines represent the linear regression line of best fit. Bar graphs below each scatter plot reflect Spearman correlation coefficients between Visit 2 pain scores and Visit 1 estimates of pain-free power at each 0.2 Hz bin within the 8-12 Hz range. For all three tests, frequency elements below 10 Hz are positively associated with pain sensitivity while frequency elements above 10 Hz are negatively associated with pain sensitivity. Asterisks (*) reflect, where applicable, significance after statistical correction for multiple tests ($\rho=0.0167$).
Figure 9B:
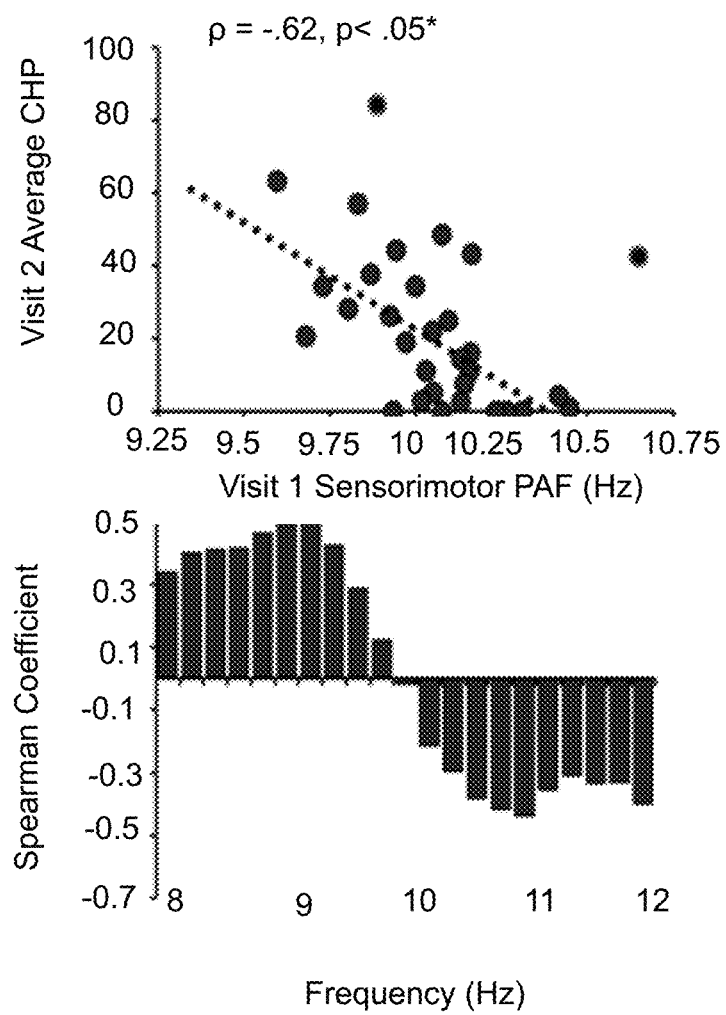
Figure 9C:
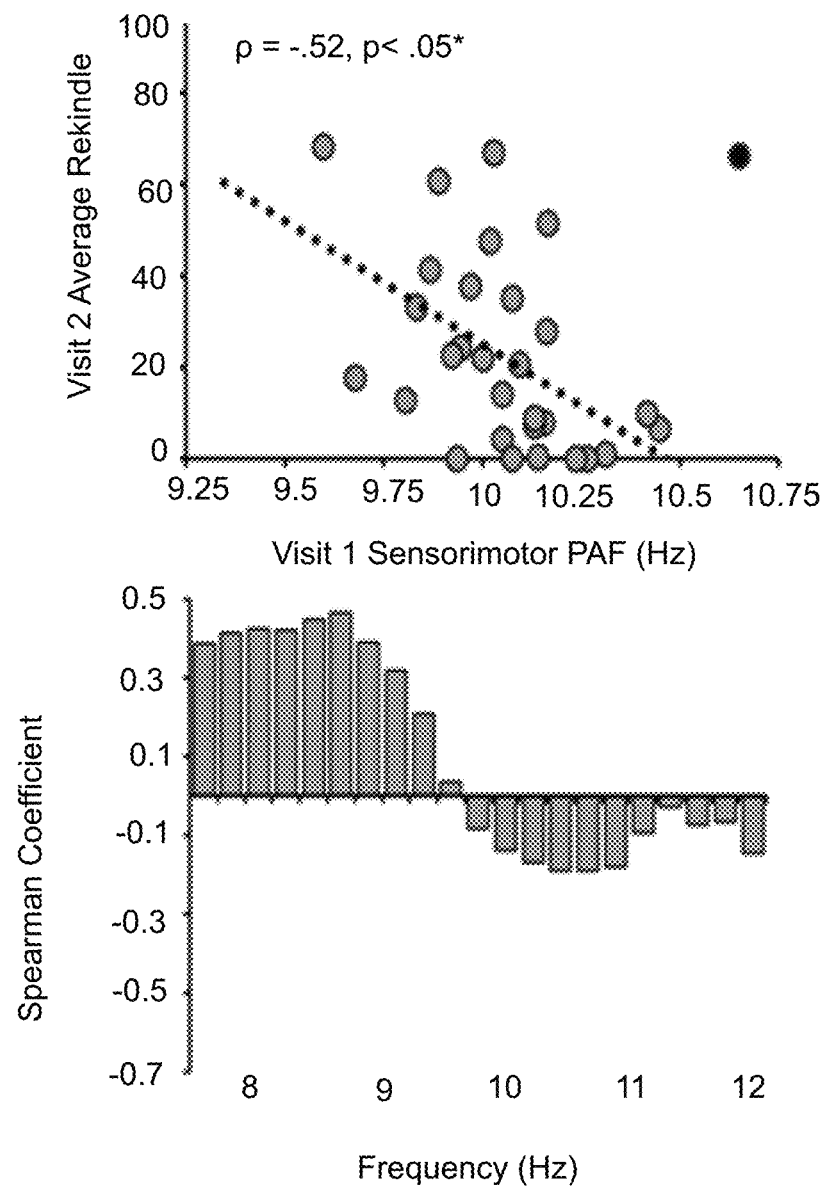

Sensorimotor Peak Alpha Frequency can Predict Thermal, Prolonged Pain Sensitivity Occurring 8 Weeks Later If pain-free, sensorimotor peak alpha frequency and prolonged pain sensitivity are stable traits, then Visit 1 peak alpha frequency should be able to predict Visit 2 pain scores collected, on average, 8 weeks later. Indeed, it was found that Visit 1 pain-free, sensorimotor peak alpha frequency and Visit 2 pain scores were strongly correlated, phasic heat pain: Spearman ρ=−0.67, ρ<0.05 corrected; Capsaicin Heat Pain: Spearman ρ=−0.62, ρ<0.05 corrected; Capsaicin Heat Pain rekindle: Spearman ρ=−0.52, ρ<0.05 corrected (FIGS. 9A-9C). For phasic heat pain, this relationship remained when for variability in thermode temperature was controlled, Spearman ρ=−.66, ρ<0.05 corrected, or included all participants regardless of pain response classification, Spearman ρ=−0.44, ρ<0.05 corrected. Expanding the peak alpha frequency calculation range to 8-12 Hz did not impact peak alpha frequency's relationship to any test, phasic heat pain: Spearman ρ=−0.57, ρ<0.05 corrected; Capsaicin Heat Pain: Spearman ρ=−0.52, ρ<0.05 corrected, Capsaicin Heat Pain rekindle: Spearman ρ=−0.45, ρ<0.05 corrected, and correlations between pain and power across the alpha range again demonstrated that the slow and fast ranges were associated with heightened and decreased pain sensitivity, respectively (FIGS. 9A-9C, lower).

Example 11

Pain-Free Sensorimotor Peak Alpha Frequency is Associated with Average Experienced Pain Three participants were removed from Study 1 for failing to develop pain in response to nerve growth factor injection. Two of these participants did not report pain in any diary entries while a third only reported pain on a single diary entry. All of the remaining 17 participants in Study 1 reported pain in at least three pain diary entries (mean=6 pain days, S.D.=3.15). One participant was removed from Study 2 for developing extreme pain (average rating=9), leaving 10 subjects in the Study 2 analyses. This value was 2.85 standard deviations above the average pain calculated from the comparable timeframes of Days 3-7 in Study 1 and Days 2 and 4 in Study 2 (group average=3.48, S.D.=1.93, range=0.67-7.00).

Figure 10A:
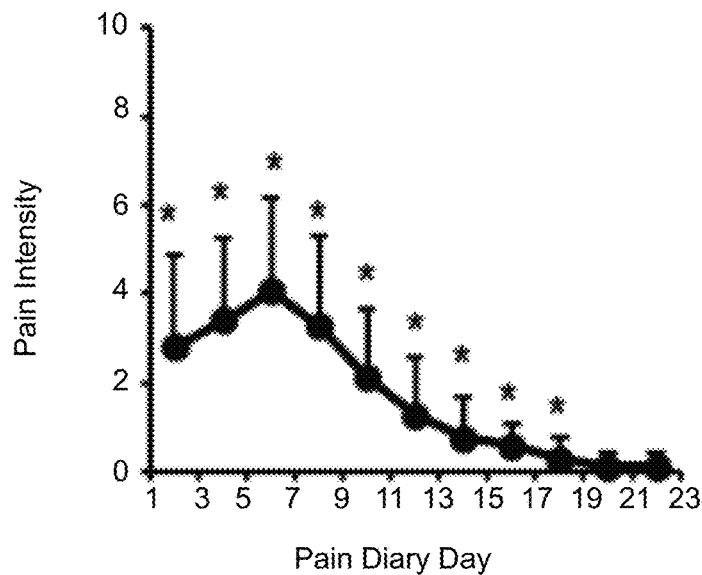
FIGS. 10A-10C shows that pain-free, sensorimotor peak alpha frequency is correlated with average nerve growth factor pain and peak alpha frequency affects the magnitude, but not the pattern, of pain development.

For Study 1, pain was present on Days 1-17, with the highest levels of pain reported on Day 5, mean=4.06, S.D.=2.11, $t_{(16)}$=7.95, ρ<0.01, and ceased on Day 19, mean=0.12, S.D.=0.33, $t_{(16)}$=1.46, ρ=0.16 (FIG. 10A). For Study 2, pain was present on both days that pain ratings were recorded, Day 2: mean=2.72, S.D.=2.12, $t_{(9)}$=4.07, ρ<0.01; Day 4: mean=2.79, S.D.=1.48, $t_{(9)}$=5.95, ρ<0.01.

Figure 10B:
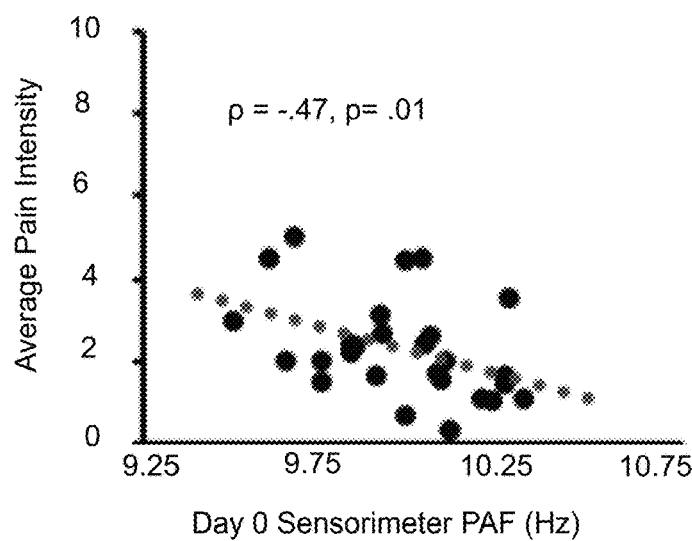

At first it was assessed whether pain-free, sensorimotor peak alpha frequency is related to nerve growth factor pain sensitivity by computing the maximum and average pain experienced over Days 1-17 for Study 1 and Days 2-4 for Study 2. Across both studies, Day 0, pain-free Sensorimotor peak alpha frequency was significantly correlated with average pain, ρ=−0.47 (Study 1 ρ=−0.39; Study 2 ρ=−0.69), ρ=0.01 (FIG. 10B). Any relationship between peak alpha frequency and maximum pain was not detected. The correlation between Day 0, pain-free Sensorimotor peak alpha frequency and average pain did not change when only Days 3, 5, and 7 were included, for Study 1 in order to best match the time-frame available for Study 2, ρ=−0.40 (Study 1 ρ=−0.35; Study 2 ρ=−0.69), ρ=0.04. This relationship was observed at nearly all EEG channels.

Average pain scores were not correlated with pain-free, sensorimotor peak alpha frequency Power (i.e. the estimated power at the peak alpha frequency), ρ<0.01 (Study 1 ρ=0.16; Study 2 ρ=−0.12), ρ>0.99. Thus, it appears that the speed of the alpha rhythm prior to nerve growth factor injection is more relevant than power for predicting pain sensitivity.

Example 12

Slow Sensorimotor Peak Alpha Frequency Individuals Consistently Experience More Nerve Growth Factor Pain Over Time Study 1 participants were separated into "Fast" and "Slow" peak alpha frequency groups based on a median split of pain-free, Sensorimotor peak alpha frequency. This yielded 8 "Slow" peak alpha frequency individuals, mean=9.79, S.D.=0.16, range=9.50-9.98, and 9 "Fast" peak alpha frequency individuals, mean=10.15, S.D.=0.12, range=9.98-10.31.

Figure 10C:
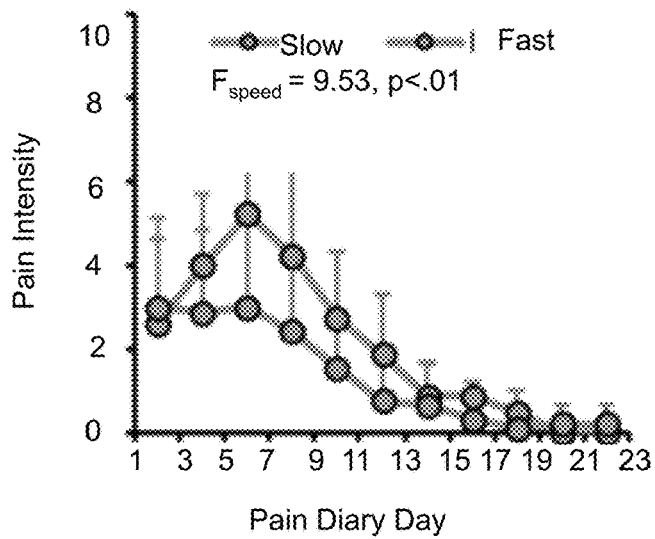

A linear mixed model with subjects as random effects and Day (repeated measures; 1, 3, 5, 7, 9, 11, 13, 15, and 17), Speed (Fast vs. Slow), and the Day×Speed interaction as fixed effects revealed a significant effect of Day, $F_{(8,22.99)}$=27.78, ρ<0.01, a significant effect of Speed, $F_{(1,38.48)}$=9.53, ρ<0.01, but no significant effect of Day×Speed, $F_{(8,22.98)}$=1.58, ρ=0.19. As can be seen in FIG. 10C, the significant effect of Speed reflects the fact that pain scores were almost universally greater for "Slow" peak alpha frequency individuals on each day following nerve growth factor injection. Failure to find a significant Days×Speed interaction reinforces the idea that peak alpha frequency distinguishes high and low pain sensitivity individuals consistently over time.

A median-split applied to Study 2 participants produced characteristically similar "Slow", n=5, mean=9.75, S.D.=0.13, range: 9.60-9.91, and "Fast" groups, n=5, mean=10.11, S.D.=0.09, range: 10.02-10.22, to what was found for Study 1. "Slow" peak alpha frequency individuals from Study 2 reported higher pain only at Day 2, however.

Example 13

Figure 11A:
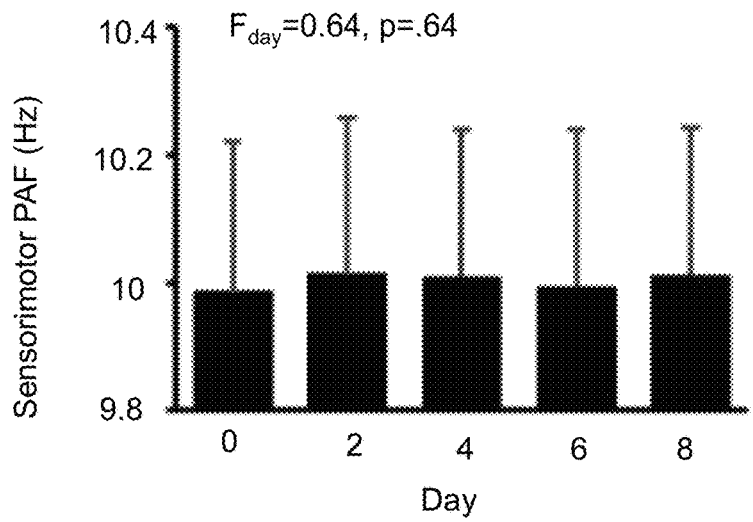
FIGS. 11A-11C shows that sensorimotor peak alpha frequency remains stable after nerve growth factor injection.
Figure 11B:
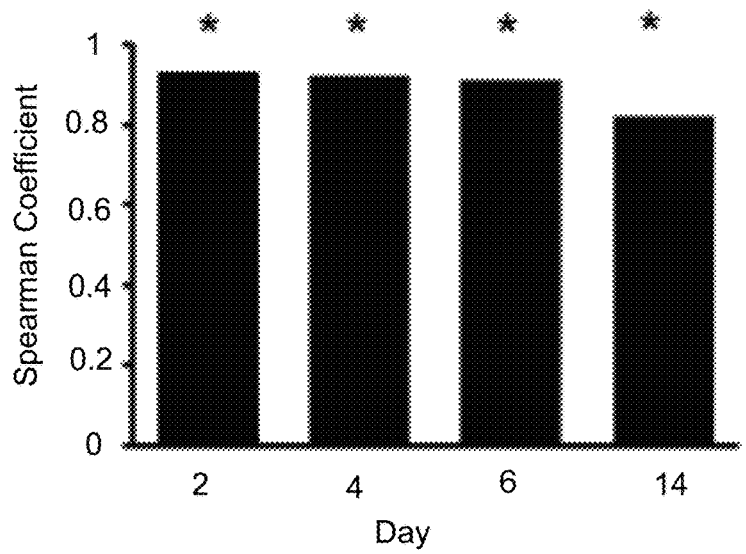

Sensorimotor Peak Alpha Frequency does not Slow after Nerve Growth Factor Injection In contrast to one's expectation that nerve growth factor injection would alter sensorimotor peak alpha frequency, a linear mixed model with subjects as random effects and Day (0, 2, 4, 6, 14) as fixed effects revealed no significant main effect of Day, $F_{(1,4)}$=0.64, ρ=0.64 (FIG. 11A). Similarly, a planned contrast comparing Day 0 peak alpha frequency, mean=9.98, S.D., =0.23, to all post-nerve growth factor peak alpha frequency estimates, mean=10.00, S.D.=0.23, was not significant, t=1.27, ρ=0.22. Finally, Bayesian analysis comparing Day 0 peak alpha frequency to average post-nerve growth factor peak alpha frequency supported the null hypothesis of no difference, Bayes Factor=0.01. As an alternative method to confirm the stability of peak alpha frequency across the experiment, correlations for all possible day pairs reached significance with no ρ value falling below 0.81 (see FIG. 11B for all Day 0 correlations). In agreement with the idea that peak alpha frequency is stable over time, peak alpha frequency estimates were nearly perfectly reliable with a Chronbach's α=0.98. In total, these results demonstrate that, despite the presence of pain, peak alpha frequency is incredibly stable over the two-weeks in which EEG was recorded.

Example 14

Figure 11C:
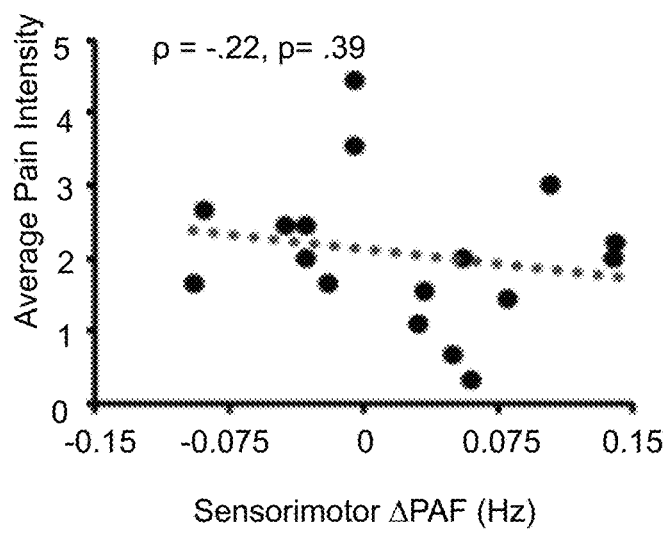

Sensorimotor Peak Alpha Frequency Shifts are Unrelated to Nerve Growth Factor Pain Sensitivity The preceding results indicate that slowing of sensorimotor peak alpha frequency does not necessarily occur during an extended period of pain. Instead, it is equally likely that an individual's peak alpha frequency will speed up (n=9) or slow down (n=8) during nerve growth factor exposure. This seems to rule against the idea that peak alpha frequency shifts are markers for the presence of pain. An alternative interpretation is that shifts in peak alpha frequency represent processes that serve to modify the intensity of the pain experience (i.e., Furman et al., 2018). To test this idea, first the difference between the average post-nerve growth factor peak alpha frequency and Day 0, pain-free peak alpha frequency (ΔPAF; positive value=faster peak alpha frequency after nerve growth factor) was calculated. The pain-free peak alpha frequency and ΔPAF were not correlated, $\rho=-0.17$, $p=0.52$, suggesting that ΔPAF may exert unique influence on pain sensitivity. However, a relationship between ΔPAF and average pain, $\rho=-0.22$, $p=0.39$ (FIG. 11C) was not found.

Example 15

Sensorimotor Peak Alpha Frequency can Identify the Most Pain Sensitive Individuals Given the high sensitivity of classification analyses to outliers, one participant with an extreme peak alpha frequency estimate was not included in either analysis (peak alpha frequency=10.65, 3.20 S.D. above the mean). In order to make the classification analysis generalizable to other datasets, and to take advantage of the strong correlation between prolonged pain tests, a composite pain sensitivity score was created by averaging scores from all three prolonged pain tests (phasic heat pain, Capsaicin Heat Pain, Capsaicin Heat Pain Rekindle). This pain sensitivity score was significantly correlated with peak alpha frequency at both Visit 1, Spearman $\rho=-0.51$, $p<0.05$, and Visit 2, Spearman $\rho=-0.60$, $p<0.05$. This relationship remained evident when all participants regardless of classification were included, Visit 1: Spearman $\rho=-0.42$, $p<0.05$; Visit 2: Spearman $\rho=-0.33$, $p<0.05$.

Figure 12A:
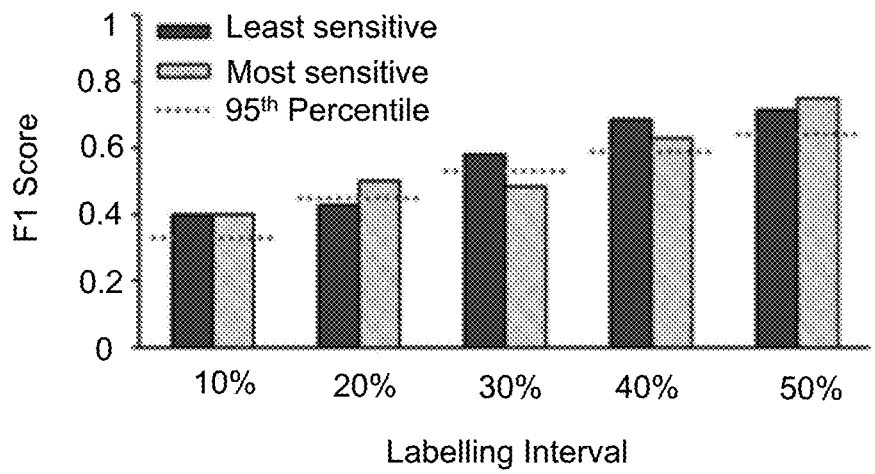
FIGS. 12A-12C shows that visit 1 pain-free, sensorimotor peak alpha frequency can accurately predict the identity of the most pain sensitive individuals and a support vector machine trained on this data can identify the most pain sensitive in an independent study.

Support vector machines (SVM) trained and tested on the current dataset were able to identify both the least and most sensitive individuals using just pain-free peak alpha frequency estimates (internal validation; details found in the Statistics section). Compared to a simulated null distribution of $F_1$ scores, the least pain sensitive individuals were identified at above chance levels at all labelling intervals but the 20% one (FIG. 12A). Similarly, the most sensitive individuals were identified at above chance levels at all labelling intervals but the 30% one. When including all participants, regardless of classification, peak alpha frequency significantly identified the least sensitive individuals at all labelling intervals but only the most sensitive individuals at the 10% and 50% intervals. This latter result likely reflects that the composite pain sensitivity score fails to capture the mixed sensitivity of Capsaicin Heat Pain non-responders to Capsaicin Heat Pain and phasic heat pain.

Figure 12B:
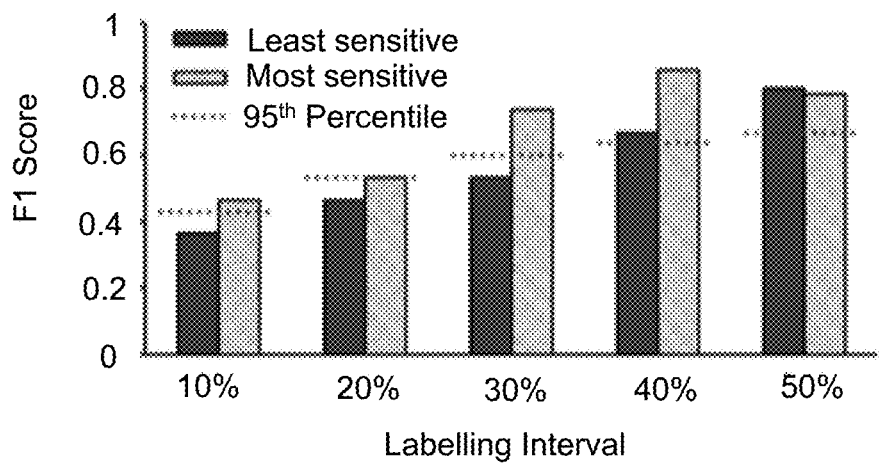

A linear SVM trained on the current dataset could identify high and low pain sensitive individuals in a separate, independent study (external validation). Using a similar procedure to one used for within-study classification, a single linear SVM trained on data from the current study was used to predict the identity of 21 participants from a previous study on Capsaicin Heat Pain sensitivity (Furman et al., 2018). Compared to a simulated null distribution of $F_1$ scores, it was found that peak alpha frequency estimates identified the most pain sensitive individuals at above chance levels for all labelling intervals and identified the least pain sensitive individuals at above chance levels only at the two largest, 40% & 50%, intervals (FIG. 12B). Rerunning the analysis with all participants, regardless of pain response classification, included in the training set yielded identical results.

Figure 12C:
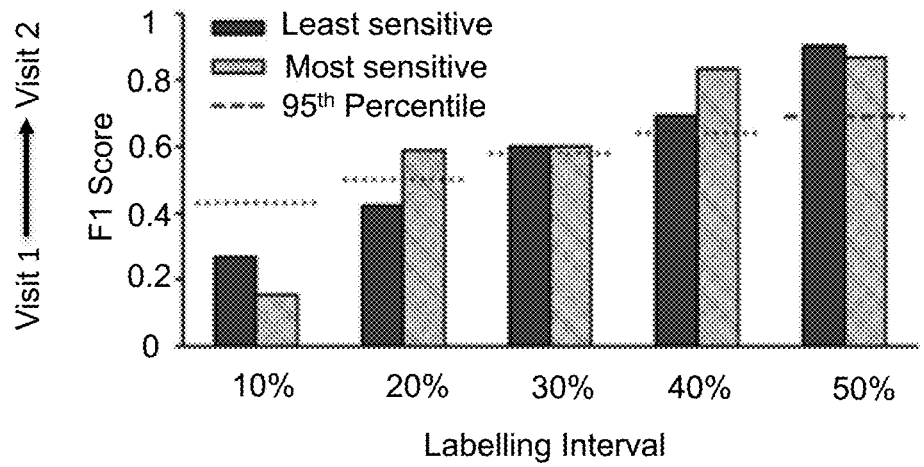

The least and most pain sensitive individuals at Visit 2 could be identified using Visit 1 pain-free, sensorimotor peak alpha frequency. Visit 2 pain sensitivity, represented as the average pain score across tests, was strongly correlated to Visit 1 pain-free, sensorimotor peak alpha frequency, Spearman $\rho=-0.66$, $p<0.05$, and remained so when including all participants regardless of pain classification, Spearman $\rho=-0.45$, $p<0.05$. Compared to a null distribution of $F_1$ scores, pain-free, sensorimotor peak alpha frequency identified the most sensitive individuals at all but the smallest labelling interval and the least sensitive individuals at all but the two smallest labelling intervals (FIG. 12C). Classification failure at the smallest labelling intervals was likely due to the relatively low number of targets available (sample=30; targets=3 and targets=6 at the 10% and 20% labelling intervals, respectively).

Rerunning the analysis with all participants, regardless of pain response classification, again demonstrated that pain-free, sensorimotor peak alpha frequency could identify the most sensitive individuals at all labelling intervals but the smallest one. For the least pain sensitive individuals, pain-free, sensorimotor peak alpha frequency failed to yield significant predictions at any labelling interval.

The following references are cited herein.
Ali, et al. Pain, 68: 401-411, 1996.
Backonja, et al. Electroencephalography and Clinical Neurophysiology 79:192-203, 1991.
Baliki, et al. Nature neuroscience 15.8:1117, 2012.
Baliki, et al. Nature Neuroscience 15:1117-1119, 2012.
Baron, R. Neuropathic Pain: A Clinical Perspective. In Sensory Nerves, (Springer, Berlin, Heidelberg), pp. 3-30, 2009.
Baum, C. et al. Perceptual and motor skills, 112(3), 926-946, 2011.
Baumann, et al., Journal of Neurophysiology 66, 212-227, 1991.
Bazanova, et al., Neuroscience & Biobehavioral Reviews 44:94-110, 2014.
Bell, A. J. and Sejnowski, T. J. Neural Computation 7:1129-1159, 1995.
Bergin, M. J. G. et al. Pain Medicine, 16(11), 2180-2191, 2015.
Brotzner, et al. Brain Res. 1577: 36-44, 2015.
Busch, et al., J. Neurosci. 29, 7869-7876, 2009.
Campbell, et al. (Pain, 141(1-2):114-118, 2009.
Cecere, et al., Current Biology 25:231-235, 2015.
Cohen, M. X. Analyzing Neural Time Series Data: Theory and Practice (MIT Press), 2014.
Culp, et al., Brain 112:1317-1331, 1989.
de Vries, et al., Journal of Pain Research 6:815-824, 2013.
Delorme, et al., Journal of Neuroscience Methods 134:9-21, 2004.
Diatchenko et al. (Human Molecular Genetics, 14(1):135-143, 2005.
Dirks, et al. The Journal of Pain, 4(3):122-128, 2003.
Foxe, et al., Neuroreport, Neuroreport. 9:3929-3933, 1998.
Foxe, J. J. and Snyder, A. C. Front Psychol 2, 2011.
Furman, et al. Neuroimage, 167:203-210, 2018.
Furman, et al. bioRxiv, 613299, 2019.
Goffaux, P. et al. Pain, 145(1-2):18-23, 2009.
Goldman, et al., Neuroreport 13:2487-2492, 2002.
Grandy, et al., Psychophysiol 50:570-582, 2013.
Hah, J. M. JAMA network open, 2(3):e190168-e190168, 2019.

Hashemi, et al., ENeuro 3, ENEURO.0275-16.2016, 2016.
Hughes, S. W. and Crunelli, V. Neuroscientist 11:357-372, 2005.
Iannetti, et al. Neuroscience, 131(1):199-208, 2005.
Jann, et al., NeuroImage 51:365-372, 2010.
Jann, et al., Brain Connectivity 2:11-20, 2012.
Jensen, O. and Mazaheri, A. Front Hum Neurosci 4, 2010.
Jin, et al., Int. J. Neurosci. 116:1035-1044, 2006.
Kalauokalani, et al. Spine, 26(13):1418-1424, 2001.
Katz, et al., Clin J Pain 12:50-55, 1996.
Keel, J. C. et al. Neurophysiology, 112(4):720-720, 2001.
Klimesch, et al., Brain Topogr 5:241-251, 1993.
Klimesch, et al., Brain Research Reviews 53:63-88, 2007.
Klimesch, W. Brain Res.Brain Res.Rev. 29:169-195, 1999.
Klimesch, W. Trends in Cognitive Sciences 16:606-617, 2012.
Koenig et al. Pain Practice, 14(3):E126-E135, 2014.
LaMotte, et al., The Journal of Physiology 448:749-764, 1992.
Lewin, et al. European Journal of Neuroscience, 4(12):1213-1218, 1992.
Lim & Dinges, Annals of the New York Academy of Sciences, 1129(1):305-322, 2008.
Lim, et al., Front Hum Neurosci 10, 2016.
Lipton, et al. In Joint European Conference on Machine Learning and Knowledge Discovery in Databases. Springer, Berlin, Heidelberg, pp. 225-239, 2014.
Liu, et al. Journal of Pain and Symptom Management, 16(1):10-20, 1998.
Llinás, et al., Trends in Neurosciences 28:325-333, 2005.
Llinás et al. PNAS, 96(26):15222-5227, 1999.
Lörincz, et al., J. Neurosci. 28:660-671, 2008.
Lörincz, et al., Neuron 63:683-696, 2009.
Lötsch, et al., Pain 156:405-414, 2015.
Malloy, & Milling, Clinical psychology review, 30(8):1011-1018, 2010.
Mathewson, et al., J. Neurosci. 29:2725-2732, 2009.
Mazaheri, et al., Hum. Brain Mapp. 30:1791-1800, 2009.
Mazaheri, et al., Biological Psychiatry 67:617-623, 2010.
Mazaheri, et al., NeuroImage 87:356-362, 2014.
Moran, et al., Front Hum Neurosci 4, 2010.
Moritz, A. R. and Henriques, F. C. (1947). Am J Pathol 23:695-720, 1947.
Naert, et al. Pain, 138(1):163-171, 2008.
Nielsen, et al. Pain, 119(1-3):65-74, 2005.
Nir, et al. Brain Research 1344:77-86, 2010.
Nir, et al. Clinical Neurophysiology 123:605-612, 2012.
Oldfield, R. C., Neuropsychologia, 9(1):97-113, 1971.
Oostenveld, et al., Clinical Neurophysiology 112:713-719, 2001.
Peng, et al. Biological Psychology 109:141-150, 2015.
Perrin, et al. Electroencephalography and clinical neurophysiology, 72(2):184-187, 1989.
Pfurtscheller, et al., Inter. Journal of Psychophysiology 24:39-46, 1996.
Ploner, et al., NeuroImage 32:1231-1236, 2006.
Ploner, et al., Trends in Cognitive Sciences 21:100-110, 2017.
Posthuma, et al., Behav Genet 31:567-579, 2001.
Price, D. D. et al. Pain, 56(2):217-226, 1994.
Romei, et al., Neuroreport 19, 203-208, 2008.
Rouder, J. N. Psychonomic bulletin & review, 16(2):225-237, 2009.
Samaha, et al., PNAS 112:8439-8444, 2015.
Sarnthein, et al., Brain, 129(1):55-64, 2005.
Schabrun, et al. Cerebral Cortex, 26(5):1878-1890, 2015.
Scheeringa, et al. Neuron 69, 572-583, 2011a.
Scheeringa, et al. The Journal of Neuroscience 31:3813-3820, 2011b.
Seminowicz, et al. Pain, 112(1-2):48-58, 2004.
Smit, et al. International Journal of Psychophysiology 61, 235-243, 2006.
Sokolova, et al., Information processing & management, 45(4):427-437, 2009.
Walls, et al. The Journal of Pain 18:S27-S28, 2017.
Walton, et al., PAIN 150:41-51, 2010.

What is claimed is:

1. A method for predicting pain sensitivity to prolonged pain in a subject, comprising the steps of:
   recording a pain-free resting state electroencephalogram of the subject;
   measuring a pain-free peak alpha frequency from the recorded pain-free resting state EEG;
   applying a prolonged pain stimulus to the subject;
   reporting, by the subject, an intensity of pain perceived during the prolonged pain stimulus; and
   comparing the pain-free peak alpha frequency with the reported intensity during the prolonged pain stimulus, wherein the pain-free peak alpha frequency correlates negatively with pain sensitivity to the prolonged pain in the subject.

2. The method of claim 1, wherein the pain-free resting state electroencephalogram is recorded from about 45 minutes to about 1 month prior to applying the prolonged pain stimulus.

3. The method of claim 1, wherein the peak alpha frequency is measured from the alpha wave spectrum component of the EEG at a frequency bandwidth from about 8 Hz to about 14 Hz.

4. The method of claim 1, wherein the peak alpha frequency is measured from the alpha wave spectrum component of the EEG at a frequency bandwidth from 9 Hz to 11 Hz.

5. The method of claim 1, wherein the pain stimulus is a heat stimulus, a cold stimulus, pressure, an electrical stimulus, a punctate stimulus, an ischemia, a muscle pain stimulus, inflammation, or a combination thereof.

6. The method of claim 5, wherein the heat stimulus is delivered by applying heat at a single temperature or by a capsaicinoid compound in combination with a thermal-contact heat stimulator or a thermode or a combination thereof.

7. The method of claim 5, wherein the muscle pain stimulus is delivered by applying an intramuscular injection of Nerve growth factor.

8. The method of claim 1, wherein the pain stimulus is delivered to an arm, a leg, a neck, a face, a viscera, a trunk or a back.

9. A method for predicting a likelihood of increased pain intensity during prolonged pain in a subject, comprising the steps of:
   recording a pain-free resting state electroencephalogram of the subject;
   applying a prolonged pain stimulus to the subject;
   recording a prolonged pain resting state electroencephalogram of the subject after an interval of time has elapsed from applying the prolonged pain stimulus;
   measuring a pain-free peak alpha frequency during the pain-free state and a prolonged pain peak alpha frequency during the prolonged pain state; and
   calculating a shift between the prolonged pain peak alpha frequency and the pain-free peak alpha frequency to obtain a peak alpha frequency shift (ΔPAF), wherein the ΔPAF correlates negatively with pain intensity during prolonged pain in the subject.

10. The method of claim 9, wherein recording the prolonged pain encephalogram is performed after the interval of about 15 minutes to about 8 weeks has elapsed.

11. The method of claim 9, wherein the peak alpha frequency is measured from the alpha wave spectrum component of the EEG at a frequency bandwidth from about 8 Hz to about 14 Hz.

12. The method of claim 11, wherein the peak alpha frequency is measured from the alpha wave spectrum component of the EEG at a frequency bandwidth from 9 Hz to 11 Hz.

13. The method of claim 9, wherein the pain stimulus is a heat stimulus, a cold stimulus, pressure, an electrical stimulus, a punctate stimulus, an ischemia, a muscle pain stimulus, an inflammation, or a combination thereof.

14. The method of claim 13, wherein the heat stimulus is delivered by applying heat at a single temperature or by a capsaicinoid compound in combination with a thermal-contact heat stimulator or a thermode or a combination thereof.

15. The method of claim 13, wherein the muscle pain stimulus is delivered by applying an intramuscular injection of Nerve growth factor.

16. The method of claim 9, wherein the pain stimulus is delivered to an arm, a leg, a neck, a face, a viscera, a trunk or a back.

17. A method for predicting a likelihood of increased pain intensity during prolonged pain in a subject, comprising the steps of:
  recording a pain-free resting state electroencephalogram of the subject;
  applying a prolonged pain stimulus to the subject;
  recording a prolonged pain resting state electroencephalogram of the subject while the prolonged pain stimulus is applied;
  measuring a pain-free peak alpha frequency during the pain-free state and a prolonged pain peak alpha frequency during the prolonged pain state; and
  calculating a shift between the prolonged pain peak alpha frequency and the pain-free peak alpha frequency to obtain a peak alpha frequency shift(ΔPAF), wherein the ΔPAF correlates negatively with pain intensity during prolonged pain in the subject.

18. The method of claim 17, wherein the peak alpha frequency is measured from the alpha wave spectrum component of the EEG at a frequency bandwidth from about 8 Hz to about 14 Hz.

19. The method of claim 18, wherein the peak alpha frequency is measured from the alpha wave spectrum component of the EEG at a frequency bandwidth from 9 Hz to 11 Hz.

20. The method of claim 17, wherein the pain stimulus is a heat stimulus, a cold stimulus, pressure, an electrical stimulus, a punctate stimulus, an ischemia, a muscle pain stimulus, or an inflammation, or a combination thereof.

21. The method of claim 20, wherein the heat stimulus is delivered by applying heat at a single temperature or a capsaicinoid compound in combination with a thermal-contact heat stimulator or a thermode or a combination thereof.

22. The method of claim 20, wherein the muscle pain stimulus is delivered by applying an intramuscular injection of Nerve growth factor.

23. The method of claim 17, wherein the pain stimulus is delivered to an arm, a leg, a neck, a face, a viscera, a trunk or a back.

* * * * *